(12) United States Patent
Chaum et al.

(10) Patent No.: US 9,700,246 B2
(45) Date of Patent: Jul. 11, 2017

(54) METHOD AND DEVICE FOR DETECTION OF BIOAVAILABLE DRUG CONCENTRATION IN A FLUID SAMPLE

(75) Inventors: Edward Chaum, Memphis, TN (US); Erno Lindner, Germantown, TN (US); Jidong Guo, Chungchun (CN)

(73) Assignees: THE UNIVERSITY OF TENNESSEE RESEARCH FOUNDATION, Knoxville, TN (US); THE UNIVERSITY OF MEMPHIS RESEARCH FOUNDATION, Memphis, TN (US)

( * ) Notice: Subject to any disclaimer, the term of this patent is extended or adjusted under 35 U.S.C. 154(b) by 737 days.

(21) Appl. No.: 13/124,036

(22) PCT Filed: Oct. 15, 2009

(86) PCT No.: PCT/US2009/060852
§ 371 (c)(1),
(2), (4) Date: Oct. 26, 2011

(87) PCT Pub. No.: WO2010/045465
PCT Pub. Date: Apr. 22, 2010

(65) Prior Publication Data
US 2012/0116195 A1    May 10, 2012

Related U.S. Application Data

(60) Provisional application No. 61/105,604, filed on Oct. 15, 2008.

(51) Int. Cl.
*A61B 5/05*    (2006.01)
*A61B 5/145*   (2006.01)
(Continued)

(52) U.S. Cl.
CPC ........ *A61B 5/14546* (2013.01); *A61B 5/1468* (2013.01); *A61B 5/4839* (2013.01);
(Continued)

(58) Field of Classification Search
CPC ..... A61B 5/145; A61B 5/14546; A61B 5/053; A61B 5/14539
(Continued)

(56) References Cited

U.S. PATENT DOCUMENTS 3,856,649 A * 12/1974 Genshaw ........... G01N 27/3335
                                                  204/418
4,053,381 A * 10/1977 Hamblen ............. G01N 27/307
                                                  204/414
(Continued)

FOREIGN PATENT DOCUMENTS

GB  WO 2006/040588  *  4/2006  .......... G01N 27/333
WO     2008/030582 A2    3/2008

OTHER PUBLICATIONS

Guo, et al. "Voltammetric Heparin-Selective Electrode Based on This Liquid Membrane with Conducting Polymer-Modified Solid Support." Analytical Chemistry. vol. 78, No. 19. Oct. 2006. pp. 6893-6902.*
(Continued)

*Primary Examiner* — Tiffany Weston
(74) *Attorney, Agent, or Firm* — Baker Donelson Bearman Caldwell & Berkowitz, P.C.; Paula Estrada de Martin

(57) ABSTRACT

The invention relates to a method for the controlled delivery of a drug as a function of bioavailable drug concentration, a sensor device for detecting bioavailable drug concentration, and a delivery device that controls delivery of the drug based on the real-time detection of bioavailable drug concentration.

7 Claims, 19 Drawing Sheets

(51) Int. Cl.
  *A61B 5/00* (2006.01)
  *A61L 29/16* (2006.01)
  *A61B 5/1468* (2006.01)
  *A61M 25/00* (2006.01)
  *A61M 31/00* (2006.01)
(52) U.S. Cl.
  CPC ........... *A61L 29/16* (2013.01); *A61B 5/14539* (2013.01); *A61B 5/6852* (2013.01); *A61L 2300/402* (2013.01); *A61L 2300/602* (2013.01); *A61M 25/0017* (2013.01); *A61M 31/00* (2013.01); *A61M 2205/3303* (2013.01)
(58) Field of Classification Search
  USPC .................. 204/412, 416, 418, 403.06, 405; 205/782.5, 782; 604/65, 503
  See application file for complete search history.

(56) References Cited

U.S. PATENT DOCUMENTS

| | | | |
|---|---|---|---|
| 4,280,494 | A | 7/1981 | Cosgrove, Jr. et al. |
| 4,533,346 | A | 8/1985 | Cosgrove, Jr. et al. |
| 4,869,264 | A | 9/1989 | Silberstein |
| 5,094,235 | A | 3/1992 | Westenskow et al. |
| 5,649,531 | A | 7/1997 | Heinonen |
| 5,830,341 | A | 11/1998 | Gilmartin |
| 6,631,291 | B2 | 10/2003 | Viertio-Oja et al. |
| 6,646,071 | B1 | 11/2003 | Klosin et al. |
| 6,691,705 | B2 | 2/2004 | Dittmann et al. |
| 6,745,764 | B2 | 6/2004 | Hickle |
| 6,757,558 | B2 | 6/2004 | Lange et al. |
| 7,108,680 | B2* | 9/2006 | Rohr .................. A61B 5/14546 604/151 |
| 7,220,240 | B2 | 5/2007 | Struys et al. |
| 7,364,552 | B2 | 4/2008 | Kiesele et al. |
| 2003/0209450 | A1 | 11/2003 | McVey et al. |
| 2003/0212441 | A1 | 11/2003 | Starkweather et al. |
| 2004/0103897 | A1 | 6/2004 | Hickle et al. |
| 2004/0217017 | A1 | 11/2004 | Kidwell |
| 2005/0022811 | A1* | 2/2005 | Kiesele ................ A61M 16/085 128/203.12 |
| 2006/0004271 | A1* | 1/2006 | Peyser et al. .................. 600/362 |
| 2006/0167722 | A1 | 7/2006 | Struys et al. |
| 2007/0060874 | A1* | 3/2007 | Nesbitt ............. A61M 5/14228 604/80 |
| 2007/0118075 | A1 | 5/2007 | Uutela et al. |
| 2007/0134721 | A1 | 6/2007 | Laitenberger et al. |
| 2007/0203448 | A1 | 8/2007 | Melker et al. |
| 2008/0000290 | A1 | 1/2008 | Nagels et al. |
| 2008/0176271 | A1 | 7/2008 | Silver et al. |
| 2008/0200789 | A1 | 8/2008 | Brister et al. |
| 2009/0177146 | A1 | 7/2009 | Nesbitt et al. |
| 2009/0277805 | A1* | 11/2009 | Amemiya ............... G01N 27/48 205/775 |
| 2010/0173421 | A1 | 7/2010 | Piletsky et al. |

OTHER PUBLICATIONS

Nablo, et al. "Sol-Gel Derived Nitric-Oxide Releasing Materials that Reduce Bacterial Adhesion." Journal of American Chemical Society. vol. 123, No. 39. 2001. pp. 9712-9713.*
Kivlehan, et al. "Toward Feedback-Controlled Anesthesia: Voltammetric Measurement of Propofol (2, 6-Diisopropylphenol) in Serum-Like Electrolyte Solutions." Analytical Chemistry. 2012. vol. 84, p. 7670-7676.*
Langmaier, et al. "Electrochemical quantification of 2, 6-diisopropylphenonl (propofol)." Analytica Chimica Acta. Oct. 17, 2011. vol. 704, Issu.*
Wang et al. "New Target Controlled Infusion Using a Hybrid Physiologically Based Pharmacokinetic Model," The 2nd International Conference on Bioinformatics and Biomedical Engineering, Shanghai, China, May 16-18, 2008, (978-1-4244-1748-3108) (EI, IEEE Xplore).

Geertsma et al. "New and Emerging Medical Technologies: A Horizon Scan of Opportunities and Risks," RIVM Report 65/07:59-63 (2007).
Toth et al. "Electrochemical Detection in Liquid Flow Analytical Techniques: Characterization and Classification," Pure Appl Chem 76(6):1119-1138 (2004).
Van Poucke et al. "Target Controlled Infusions: Targeting the Effect Site While Limiting Peak Plasma Concentration," IEEE Transactions on Biomedical Engineering 51(11):1869-1875 (2004).
Enlund, Mats "TCI: Target Controlled Infusion, or Totally Confused Infusion? Call for an Optimised Population Based Pharmacokinetic Model for Propofol," Upsala J Med Sci 113(2):161-170 (2008).
Sreevastava et al. "Automated Target Controlled Infusion Systems: The Future of Total Intravenous Anaesthesia," MJAFI 64:261-262 (2008).
Casati et al. "Clinical Assessment of Target-controlled Infusion of Propofol During Monitored Anesthesia Care," Can J Anesth 46(3):235-239 (1999).
Leslie et al. "Target-controlled Infusion Versus Manually-controlled Infusion of Propofol for General Anaesthesia of Sedation in Adults," Cochrane Database of Systematic Reviews 3:1-33 (2008).
Viviand et al. "Induction and Maintenance of Intravenous Anaesthesia Using Target-controlled Infusion Systems," Best Practice & Research Clinical Anaesthesiology 15(1):19-33 (2001).
Diprifusor manual: Target Controlled Infusion (TCI) in Anaesthetic Practice, AstraZeneca pp. 1-59 (1999).
PCT International Search Report and Written Opinion for PCT/US2009/060852 mailed Dec. 2, 2009.
European Search Report for corresponding European Application No. 09821258.2 (mailed Oct. 30, 2014).
Yun et al., "Clinical Application of Disposable Heparin Sensors—Blood Heparin Measurements During Open Heart Surgery," ASAIO J. 41:M661-M664 (1995).
Arumugam et al., "Wafer-scale fabrication of patterned carbon nanofiber nanoelectrode arrays: A route for development of multiplexed, ultrasensitive disposable biosensors," Biosensors Bioelectronics 24(9): 2818-2824 (2009).
Blanco et al. "Microfluidic-optical integrated CMOS compatible devices for label-free biochemical sensing." Journal of Micromechanics and Microengineering 16.5 (2006): 1006.
Chen et al. "A bonding technique using hydrophilic SU-8." Journal of Micromechanics and Microengineering 17.10 (2007): 1978.
Delamarche et al. "Stability of molded polydimethylsiloxane microstructures." Advanced Materials 9.9 (1997): 741-746.
Fletcher et al. "Transfer of Flexible Arrays of Vertically Aligned Carbon Nanofiber Electrodes to Temperature-Sensitive Substrates." Advanced Materials 18.13 (2006): 1689-1694.
Glen. "The development of 'Diprifusor': a TCI system for propofol." Anaesthesia 53.s1 (1998): 13-21.
Gray et al. "Development of the technology for 'Diprifusor' TCI systems." Anaesthesia 53.s1 (1998): 22-27.
Guillorn et al. "Individually addressable vertically aligned carbon nanofiber-based electrochemical probes." Journal of Applied Physics 91.6 (2002): 3824-3828.
Huang et al. "Microelectrode arrays for electrochemistry: Approaches to fabrication." Small 5.7 (2009): 776-788.
Lee et al. "An aqueous-based surface modification of poly (dimethylsiloxane) with poly (ethylene glycol) to prevent biofouling." Langmuir 21.25 (2005): 11957-11962.
McDonald et al., "Fabrication of Microfluidic Systems in poly(dimethylsiloxane)," Electrophoresis 21:27-40 (2000).
McKnight et al. "Effects of microfabrication processing on the electrochemistry of carbon nanofiber electrodes." The Journal of Physical Chemistry B 107.39 (2003): 10722-10728.
Melechko et al. "Vertically aligned carbon nanofibers and related structures: controlled synthesis and directed assembly." Journal of applied physics 97.4 (2005): 041301.
Mijatovic et al. "Technologies for nanofluidic systems: top-down vs. bottom-up—a review." Lab on a Chip 5.5 (2005): 492-500.
Nordstrom et al. "Rendering SU-8 hydrophilic to facilitate use in micro channel fabrication." Journal of Micromechanics and Microengineering 14.12 (2004): 1614.

(56) References Cited

OTHER PUBLICATIONS

Potje-Kamloth et al. "Electrochemically prepared insulation for carbon fiber microelectrodes." Berichte der Bunsengesellschaft für physikalische Chemie 93.12 (1989): 1480-1485.
Unger et al. "Monolithic microfabricated valves and pumps by multilayer soft lithography." Science 288.5463 (2000): 113-116.
Willmann et al. "PK-Sim®: a physiologically based pharmacokinetic 'whole-body' model." Biosilico 1.4 (2003): 121-124.
Ymeti et al. "Integration of microfluidics with a four-channel integrated optical Young interferometer immunosensor." Biosensors and Bioelectronics 20.7 (2005): 1417-1421.
Lund et al, Organic Electrochemistry, 4th Revised and Expanded Revision, Marcel Dekker, Inc, New York, 2001.

\* cited by examiner

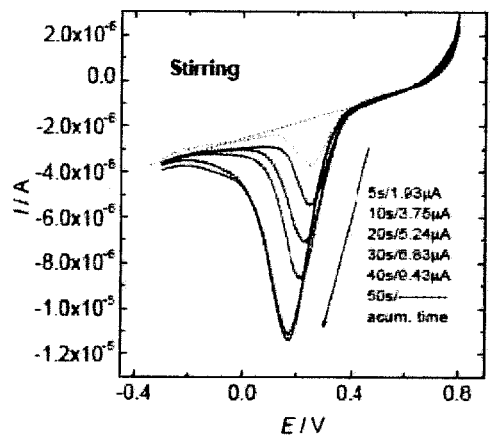
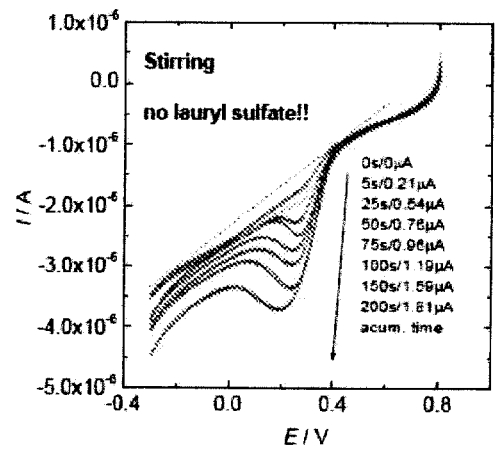
Figure 17
Figure 18
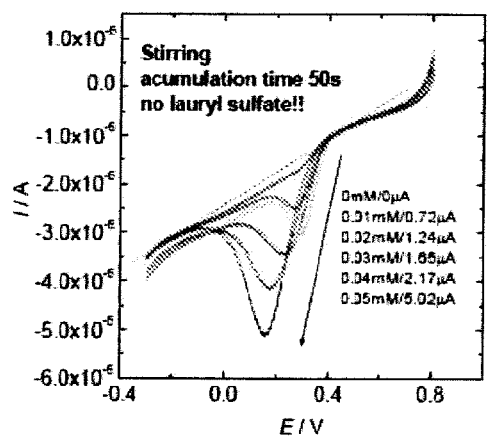
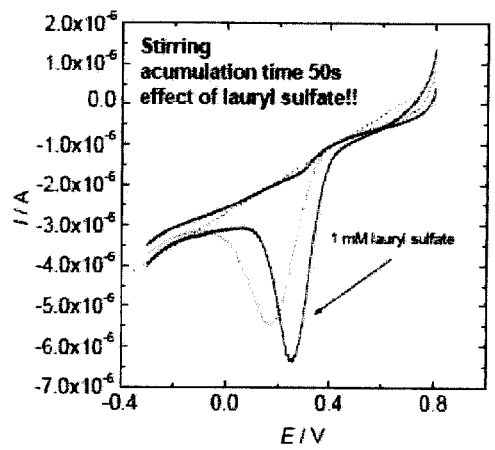
Figure 19
Figure 20

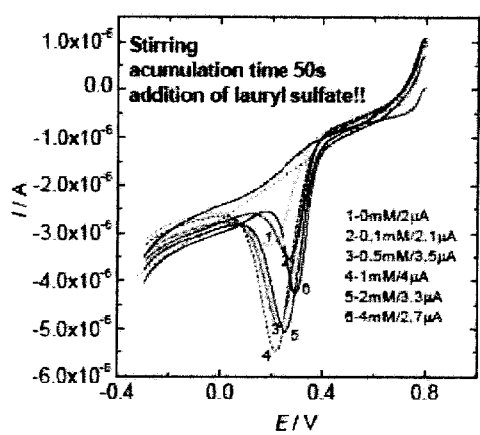
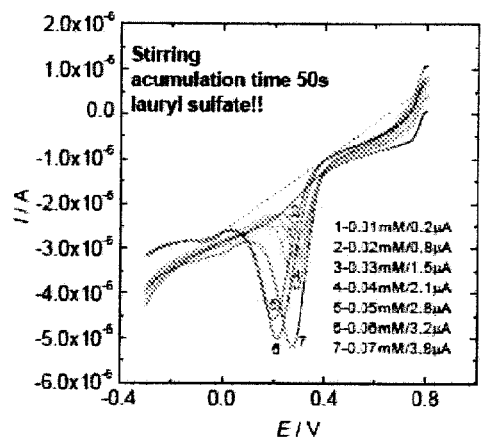
Figure 21          Figure 22
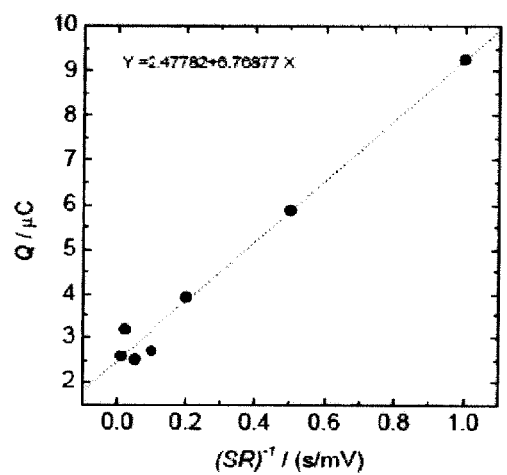
Figure 23

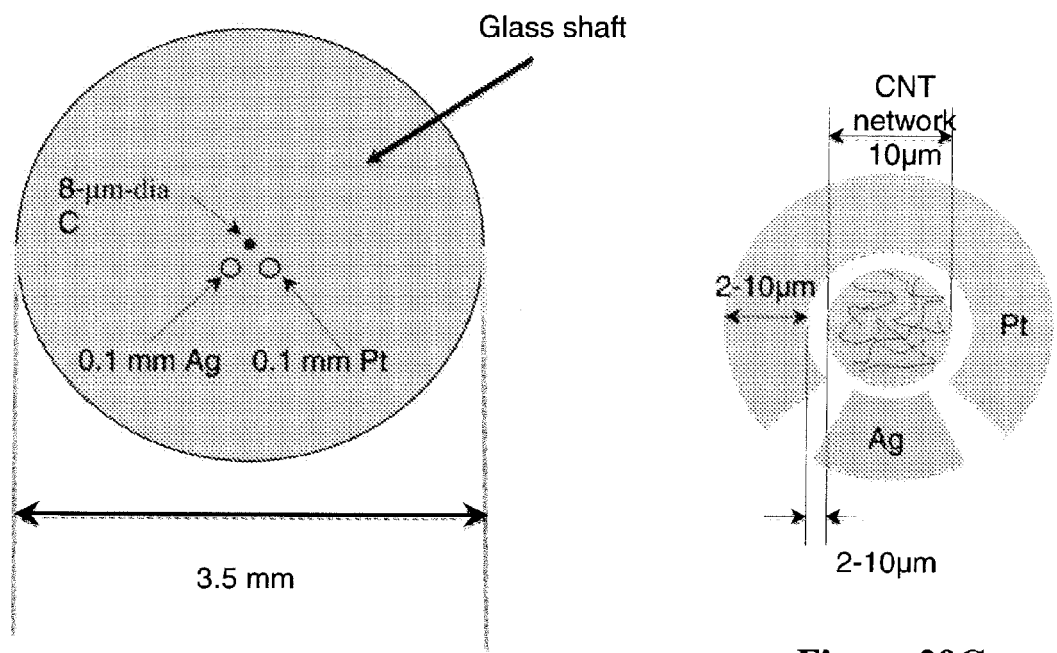
Figure 29A
Figure 29C
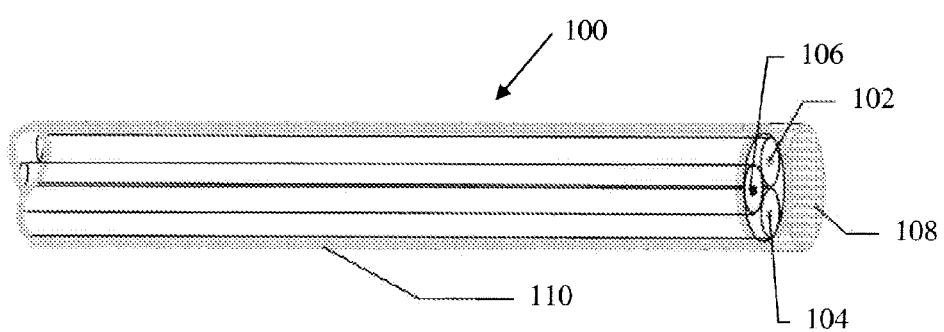
Figure 29B

METHOD AND DEVICE FOR DETECTION OF BIOAVAILABLE DRUG CONCENTRATION IN A FLUID SAMPLE

CROSS-REFERENCE TO RELATED APPLICATIONS

This application is a national stage application under 35 U.S.C. 371 from PCT Application No. PCT/US09/60852, filed Oct. 15, 2009, which claims the benefit of U.S. Provisional Patent Application Ser. No. 61/105,604, filed Oct. 15, 2008, which is hereby incorporated by reference in its entirety.

STATEMENT OF GOVERNMENT SPONSORSHIP

The present invention was made with funding received from the U.S. Army under grant W81XWH-050200064. The government has certain rights in this invention.

FIELD OF THE INVENTION

The invention relates to a method for the controlled delivery of a drug as a function of bioavailable drug concentration, a sensor device for detecting bioavailable drug concentration, and a delivery device that controls delivery of the drug based on the real-time detection of bioavailable drug concentration.

BACKGROUND OF THE INVENTION

Computer-controlled infusion pumps, the delivery functions of which are typically determined by means of a pharmacokinetic ("PK") model, are known according to the prior art as Target Controlled Infusion ("TCI") devices and are commercially available. The main application field of TCI is the control of intravenously administered narcotics (for example Propofol, marketed as Diprifusor™ by Astra-Zeneca (Product information "Diprifusor™: Target Controlled Infusion (TCI) in anaesthetic practice", AstraZeneca Anaesthesia, New Edition (1998)). A disadvantage of these known methods is that the pharmacokinetic model is a three-compartment model fitted to experimental plasma data. With such a "black-box" method, there is no opportunity for the patient's individual drug-response to be considered.

Modifications to these TCI devices include the consideration of one or more physiological factors in combination with the PK model. The physiology-based pharmacokinetic/pharmacodynamic ("PK/PD") models such as PK-Sim® developed by Bayer Technology Services GmbH (Willmann et al., "PK-Sim®: A Physiologically Based Pharmacokinetic 'Whole-body' Model," *Biosilico* 1:121-124 (2003)), makes it possible to describe the influence of individual physiological and anatomical parameters such as organ size and composition, blood flow rates, etc., on the pharmacokinetic behavior of drugs as a function of time. These physiological and anatomical parameters can in turn be attributed to a few easily measurable quantities such as body weight and body mass index.

The exact dosage of a drug as a function of time is crucial for the safety and success of the treatment in many indication fields (e.g., anesthesia, diabetes, shock, sepsis, cardiovascular failure, asthma, and cancer). With the aid of electronically controlled infusion pumps, drugs can be administered with an arbitrarily predetermined time-variable rate. The resulting concentration-time profile and effect-time profile do not depend only on the dosage profile, however, but are essentially determined by the PK and PD properties of the drug in question. Physiology-based PK and PD computer models are only capable of simulating the concentration-time profile as well as the effect-time profile of a drug in a patient's body. They are, simply, an approximation.

Thus, there remains a need for a sensor device that can accurately detect bioavailable drug concentration, and a drug delivery device that includes such a sensor device for controlling drug delivery, in real-time, based upon detected bioavailable drug concentration.

The present invention is directed to overcoming these and other deficiencies in the art.

SUMMARY OF THE INVENTION

A first aspect of the present invention relates to an electrochemical sensor that includes two or more electrodes, and a coating that surrounds the two or more electrodes, wherein the coating comprises a structural component, a water immiscible organic solvent, and a charge transfer component, and wherein the coating selectively partitions an electrochemically active drug such that an oxidation/reduction current within the coating can be measured (via the two or more electrodes).

A second aspect of the present invention relates to an indwelling catheter that includes a body and a lumen, and one or more electrochemical sensors secured in the body with at least a portion of the sensors being in communication with either the lumen or externally of the body (such that the sensor(s) are exposed to the interior of a blood vessel). According to a preferred embodiment, the catheter contains one or more electrochemical sensors according to the first aspect of the present invention. According to another preferred embodiment, the catheter contains a sensor array that includes a plurality of working electrodes.

A third aspect of the present invention relates to a target-controlled infusion drug delivery device that includes a drug reservoir; a pump in communication with the drug reservoir; an electrochemical sensor or sensor array, the electrochemical sensor(s) comprising one or more electrodes and being capable of detecting a bioavailable drug concentration in a fluid sample; and a control system that receives output of the electrochemical sensor(s) upon detection of a bioavailable drug concentration in the fluid sample and controls operation of the pump based on the detected concentration of bioavailable drug.

A fourth aspect of the present invention relates to a method of modulating drug delivery that includes the steps of: exposing a fluid sample obtained from a patient to an electrochemical sensor comprising one or more electrodes, the electrochemical sensor capable of detecting a bioavailable drug concentration in a fluid sample; detecting an oxidation/reduction current during said exposing, wherein the detected current relates to a concentration of bioavailable drug in the fluid sample; and modulating delivery of the drug into a patient based on the concentration of the bioavailable drug in the fluid sample.

According to this aspect of the invention, the electrochemical sensor can be in the form of a sensor according to the first aspect of the present invention or a sensor array comprising a plurality of working electrodes and one or more additional electrodes, whereby the sensor or sensor array is capable of detecting a bioavailable drug concentration in a fluid sample from the patient. The sensor or sensor array can be positioned ex vivo or in vivo.

A fifth aspect of the present invention relates to a method for electrochemical detection of bioavailable drug concentration in a fluid sample, the method including the steps of exposing a fluid sample to an electrochemical sensor comprising one or more electrodes and a coating that surrounds the one or more electrodes, which coating is capable of partitioning the bioavailable drug directly from the fluid sample; and detecting an oxidation/reduction current during said exposing, wherein the detected current relates to the concentration of bioavailable drug in the fluid sample.

A sixth aspect of the present invention relates to a method for electrochemical detection of bioavailable drug concentration in a fluid sample, the method including the steps of exposing a fluid sample to an electrochemical sensor array comprising a plurality of working electrodes and one or more additional electrodes; and detecting an oxidation/reduction current during said exposing, wherein the detected current relates to the concentration of bioavailable drug in the fluid sample. By virtue of the array comprising the plurality of working electrodes, the detecting is intended to be carried out repeatedly with a different working electrode during each step.

These methods of electrochemical detection of bioavailable drug concentration are intended to be used to modify the delivery rate of the drug to a patient during real-time.

The accompanying Examples demonstrate that the drug Propofol ("DIPP") can be detected in acidic solutions in vitro and can be quantified down to a concentration as low as $1 \times 10^{-6}$M, which is within the therapeutic dose range of the drug for its use as a general anesthetic agent. It has also been determined that the accuracy of DIPP signal detection and signal intensity is influenced by several features of the electrochemical method, including pH and composition of the solution, voltage scan rate, presence and optimal concentration of detergents, agitation of the solution during quantitation, and the deposition of biofilms/electrode fouling. The Examples further demonstrate that an accurate quantification of DIPP can be obtained within 30 seconds using this method and that a robust signal is seen at therapeutic and sub-therapeutic levels using cyclic voltammetry. The ability to measure therapeutic levels using microfabricated thin film microelectrodes and nanoelectrode arrays demonstrate different approaches for overcoming the problem of biofouling. In particular, the coated electrodes are capable of partitioning free (bioactive) DIPP into the organic sensor membrane from complex solutions, removing chloride ion interference from the detection of DIPP in salt-containing solutions, and are free from interference with other molecules such as acetaminophen (Tylenol®) and Vitamin C. Sensor arrays overcome the problem using a plurality of working electrodes, such that for each sensing event a new working electrode is employed. These results will allow for construction of an indwelling sensor or ex vivo microfluidic sensor for use in closed-loop control systems that integrate into TCIA biosensor for delivery of DIPP.

BRIEF DESCRIPTION OF THE DRAWINGS

FIG. 17 is a stripping voltammogram of $10^{-4}$M DIPP in $10^{-2}$M $H_2SO_4$+$10^{-3}$M sodium lauryl sulfate using acum. at 0.8V strip 100 mV/s to −0.3V, with stirring. The DIPP was introduced from a 0.01M solution in 0.1M NaOH water. Working electrode=glassy carbon; counter electrode=Pt; and reference electrode=Ag/AgCl.

FIG. 18 is a stripping voltammogram of $10^{-5}$M DIPP in $10^{-2}$M $H_2SO_4$+$10^{-3}$M sodium lauryl sulfate using acum. at 0.8V strip 100 mV/s to −0.3V, with stirring. The DIPP was introduced from a 0.01M solution in 0.1M NaOH water. Working electrode=glassy carbon; counter electrode=Pt; and reference electrode=Ag/AgCl.

FIG. 19 is a stripping voltammogram of 1, 2, 3, 4, $5 \times 10^{-5}$M DIPP in $10^{-2}$M $H_2SO_4$ without sodium lauryl sulfate using acum. at 0.8V strip 100 mV/s to −0.3V, with stirring. The DIPP was introduced from a 0.01M solution in 0.1M NaOH water. Working electrode=glassy carbon; counter electrode=Pt; and reference electrode=Ag/AgCl.

FIG. 20 is a stripping voltammogram of $6 \times 10^{-5}$M DIPP in $10^{-2}$M $H_2SO_4$+$10^{-3}$M sodium lauryl sulfate using acum. at 0.8V strip 100 mV/s to −0.3V, with stirring. The DIPP was introduced from a 0.01M solution in 0.1M NaOH water. Working electrode=glassy carbon; counter electrode=Pt; and reference electrode=Ag/AgCl.

FIG. 21 is a stripping voltammogram of $4 \times 10^{-5}$M DIPP in $10^{-2}$M $H_2SO_4$+0.1, 0.5, 1.2, $2.4 \times 10^{-3}$M sodium lauryl sulfate using acum. at 0.8V strip 100 mV/s to −0.3V, with stirring. The DIPP was introduced from a 0.01M solution in 0.1M NaOH water. Working electrode=glassy carbon; counter electrode=Pt; and reference electrode=Ag/AgCl.

FIG. 22 is a stripping voltammogram of $1-7 \times 10^{-5}$M DIPP in $10^{-2}$M $H_2SO_4$+$10^{-3}$M sodium lauryl sulfate using acum. at 0.8V strip 100 mV/s to −0.3V, with stirring. The DIPP was introduced from a 0.01M solution in 0.1M NaOH water. Working electrode=glassy carbon; counter electrode=Pt; and reference electrode=Ag/AgCl.

FIG. 23 is a graph showing the relationship between the charge under the DIPP stripping peak and the voltage scan rate for stripping under the conditions of $4 \times 10^{-5}$M DIPP in $10^{-2}$M $H_2SO_4$+$10^{-3}$M sodium lauryl sulfate using acum. at 0.8V strip 100 mV/s to −0.3V, with stirring. The DIPP was introduced from a 0.01M solution in 0.1M NaOH water. Working electrode=glassy carbon; counter electrode=Pt; and reference electrode=Ag/AgCl.

FIGS. 29A-C illustrate fabricated microelectrode designs, specifically the capillary array with sensors embedded in a coating (29A-B) and lithography design (29C).

DETAILED DESCRIPTION OF THE INVENTION

Figure 1:
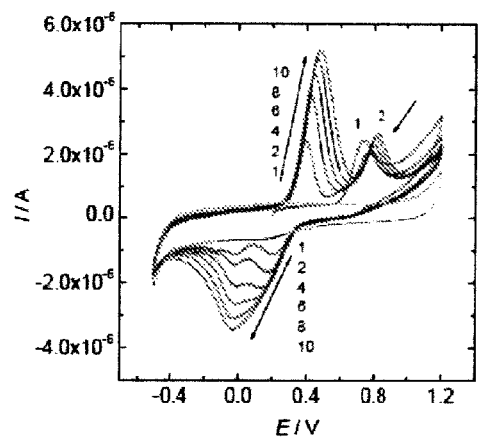
FIG. 1 is a cyclic voltammogram of $10^{-4}$M DIPP in $10^{-2}$M $H_2SO_4$ using 100 mV/s scan, 10 cycles. The DIPP was introduced from a 0.01M solution in 0.1M NaOH water. Working electrode=glassy carbon; counter electrode=Pt; and reference electrode=Ag/AgCl.

The present invention relates to electrochemical sensors for the detection of bioavailable drug concentration, and devices and methods that include or utilize the electrochemical sensors for real-time control over the delivery of a drug based on the bioavailable drug concentration.

As used herein, the term "real-time" is intended to mean a response that it carried out within less than a minute, preferably less than 20 or 10 seconds, and most preferably within about 1 to about 5 seconds following a detection event.

As used herein, the term "fluid sample" is intended to mean a body fluid sample including, without limitation blood, plasma, cerebrospinal fluid, and other body fluids.

As used herein, the term "bioavailable drug concentration" is intended to mean the concentration of a drug that exists in a fluid sample but remains unbound by plasma proteins. Any of a variety of electrochemically active drugs can be monitored in accordance with the present invention, including anesthetics, barbiturates, and sedatives. Exemplary electrochemically active drugs include, without limitation, Propofol, midazolam, methohexital, etomidate, and sufentanil.

Accordingly, a first aspect of the present invention relates to an electrochemical sensor or sensor array that can be used to detect bioavailable drug concentration from a fluid sample.

One preferred embodiment of the electrochemical sensor includes two or more electrodes, and a coating that surrounds the two or more electrodes, where the coating is capable of selectively partitioning an electrochemically active drug directly from the fluid sample such that an oxidation/reduction current within the coating can be measured by the two or more electrodes. The coating also effectively partitions a biocompatible interface between the electrochemical sensor and a sample fluid, and/or prevents electrode fouling (because biological molecules in the fluid sample do not directly contact the electrodes in this embodiment).

By way of example, FIGS. 29A-B illustrate a microelectrode sensor 100 that includes a reference electrode 102, a counter electrode 104 and a working electrode 106, each of which have at least one end surrounded with a coating 108 through which one or more molecules of the bioavailable drug can be partitioned. The electrodes are housed in a glass capillary 110, the end of which has been removed to expose the electrodes. Alternatively, coating 108 may cover or surround more than the tip of reference electrode 102, counter electrode 104 and working electrode 106, for example, the whole of electrochemical sensor 100 could be embedded in the coating material.

The coating 108 preferably contains a structural component, a water immiscible organic solvent, and a charge transfer component. The coating 108 may optionally contain one or more further additives including, without limitation, a membrane resistance controlling component and a biocompatibility enhancing component.

Any suitable structural component can be utilized in the coating 108. The structural component can be polymeric or non-polymeric. Exemplary structural components include, without limitation, polyvinylchloride (PVC), silicone rubber, polyurethane, (meth)acrylate polymer, polypyrrole, polythiophene, polyoctylthiophene, polyanaline, polyvinyl pyrrolidone, agarose, hydrogel, sol-gel materials, and combinations thereof.

Any suitable water immiscible organic solvent can be utilized in the coating 108. The organic solvent is responsible for assisting in the partitioning of the bioavailable drug from the fluid sample into the coating 108. Exemplary water immiscible organic solvents include, without limitation, 2-nitrophenyl octyl ether (o-NPOE), dioctyl sebacate (DOS), bis(2-ethylhexyl) sebacate, benzyl s-nitrophenyl ether, bis(1-butilpentyl) adipate, bis(2-ethylhexyl) adipate, bis(2-ethylhexyl) phthalate, 1-chloronaphthalene, chloroparaffin, 1-decanol, dibutyl phthalate, dibutil sebacate, dibutyl-dilaurate, dodecyl 2-nitrophenyl ether, and combinations thereof.

Any suitable charge transfer agent can be utilized in the coating 108. Exemplary charge transfer components include, without limitation, tetradecylammonium tetrakis (pentofluorophenyl)borate (TDATPFPB), tetrahexylammonium perchlorate, and combinations thereof.

Any suitable membrane resistance controlling agent can be utilized in the coating 108, when desired. Exemplary membrane resistance controlling agents include, without limitation, lipophilic electrolytes, tetradodecyl ammoniumtetrakis(4-chlorophenyl) borate (ETH500), bis(triphenylphoranylidene) ammonium tetrakis[3,5-bis(trifluoromethyl) phenyl]borate (BTPPATFPB), and combinations thereof.

Any suitable biocompatibility enhancing component can be utilized in the coating 108, when desired. Exemplary biocompatibility enhancing components include, without limitation, nitric-oxide releasing sol-gel materials, N-(6-aminohexyl)aminopropyltrimethoxysilane, balanced isobutyltrimethoxysilane diazeniumdiolate, and combinations thereof.

According to one preferred embodiment, the coating 108 is formed from a composition including about 15 to about 67 wt percent PVC, about 33 to about 85 wt percent o-NPOE, and about 0.001 to about 15 wt percent TDATPFPB.

Coating 108 can be of a suitable dimension that affords effective partitioning while allowing for sufficient oxidation/reduction current within coating 108. For example, and not by limitation, coating 108 is less than about 200 µm thick, more preferably less than about 100 µm thick. According to one embodiment, coating 108 has a sub-micron thickness. According to another embodiment, coating 108 is between about 1 to about 25 µm thick.

Reference electrode 102, counter electrode 104 and working electrode 106 can be formed out of a suitable conductive material including, without limitation, carbon, gold, platinum, palladium, ruthenium, rhodium or combinations thereof. Although only three microelectrodes—reference electrode 102, counter electrode 104 and working electrode 106 are described with respect to FIG. 29B, according to certain embodiments four electrodes can be present. Further, various aspects of the invention are not limited by specific arrangement and structure of reference electrode 102, counter electrode 104 and working electrode 106 shown in FIG. 29B, and one skilled in the art after reading this disclosure may devise other arrangements and structures. Exemplary electrode functions include, working electrode, auxiliary or counter electrode, and reference electrode. The particular function and number of electrodes will depend upon the type of electrochemical sensor 100 that is employed, and aspects of the present invention are not limited by specific formation(s) of electrochemical sensor 100.

Exemplary sensor formats include, without limitation, voltammetric sensors, potentiometric sensors, conductometric sensors, and coulometric sensors. A voltammetric sensor can include, without limitation, one or more working electrodes in combination with a reference electrode, or one or more working electrodes in combination with a reference electrode and a counter electrode. In voltammetry, the potential applied to the working electrode is varied over time to measure the current through either the coating (i.e., for the coated sensor embodiment) or in the fluid sample (i.e., for the uncoated sensor array embodiment). A conductometric sensor can include two or four electrodes, which measure the impedance of either the coating or the fluid sample. A potentiometric cell can include two electrodes, in which the potential of the indicator electrode is measured at zero current. A coulometric sensor can include two or more electrodes. The design and principles surrounding these types of electrochemical sensors are described in Toth et al., "Electrochemical Detection in liquid Flow Analytical Techniques: Characterization and Classification," *Pure Appl. Chem.* 76(6):1119-1138 (2004), which is hereby incorporated by reference in its entirety.

Another preferred embodiment of the electrochemical sensor includes two or more electrodes in an electrode array. One form of construction includes a plurality of working electrodes, which are used in series such that each working electrode is used, preferably, only one or twice, more preferably only once. This has the benefit of providing a new working electrode during each sensing process, and therefore biofouling of a working electrode (via proteins and other biomolecules in the fluid sample) is immaterial. The sensor according to this embodiment may include one or both of an auxiliary or counter electrode, and a reference electrode. An exemplary construction of this embodiment is illustrated in FIG. 40, and its use is described in Example 3 infra.

Another form of construction includes a plurality of sensor arrays, where each array includes the two or more electrodes required for the sensing format of choice, e.g., one or more working electrodes in combination with a reference electrode and a counter electrode for voltammetry. FIG. 40 illustrates a microfluidic device 200 that includes a microfluidic channel 202 and a plurality of carbon nanofiber sensors 204 in array within the channel 202. One or more sensor arrays can be provided in each of a plurality of microfluidic channels.

Carbon nanofibers are compatible with a large number of microfabrication techniques including lithographic processing, material lift-off techniques, wet and dry etching, and chemical/mechanical polishing. As such, standard microfabrication techniques may be employed to incorporate into functional nanoscale electroanalytical platforms. Single CNFs can be synthesized on electrical interconnects and implemented as electrochemical electrodes with individual addressability down to ~1-2 micron interfiber spacing (Arumugam et al., "Wafer-scale fabrication of patterned carbon nanofiber nanoelectrode arrays: A route for development of multiplexed, ultrasensitive disposable biosensors," *Biosensors Bioelectronics* 24(9): 2818-2824 (2009); Melechko et al., "Vertically aligned carbon nanofibers and related structures: Controlled synthesis and directed assembly," *J. Appl. Phys.* 97(4):041301 (2005), each of which is hereby incorporated by reference in its entirety). Alternatively, the carbon nanofiber array can be prepared on a flexible substrate and then introduced to the interconnect (Fletcher et al., "Transfer of Flexible Arrays of Vertically Aligned Carbon Nanofiber Electrodes to Temperature-Sensitive Substrates," *Adv. Mat.* 18(13):1689-1694 (2006), which is hereby incorporated by reference in its entirety). Moreover, fabrication techniques allow only the nanoscale tip of these fibers to be electrochemically active (Huang et al., "Microelectrode Arrays for Electrochemistry: Approaches to Fabrication," *Small* 5(7):776-788 (2009); Potje-Kamloth et al., "Electrochemically Prepared Insulation for Carbon Fiber Microelectrodes," *Berichte der Bunsengesellschaft für Physikalische Chemie* 93(12):1480-1485 (1989), each of which is hereby incorporated by reference in its entirety). Thus, the nanofiber serves both to elevate the electroanalytical measurement volume above the planar substrate and to electrically bridge between the nanoscale dimensions of the fiber tip and the microscale dimensions of the electrical interconnects of the substrate. The electroactive tips of these vertically-oriented devices enable electroanalytical probing of extremely small volumes (<500 zeptoliter). This enables both the quantification of electroactive species as well as the direct manipulation of the local environment (oxidation, reduction, pH variation, field application, thermal modulation). These CNF probes can also be integrated with an active matrix thin film transistor array to significantly improve functionality and significantly increase the number of electrochemically active probes (400 probes in a 20×20 array, 1 mm$^2$ footprint). This adds significant parallelism, offering high device density, large dynamic driving range, high temporal and electrophysiological signal sensitivity, and simpler driving electronics.

Figure 40:
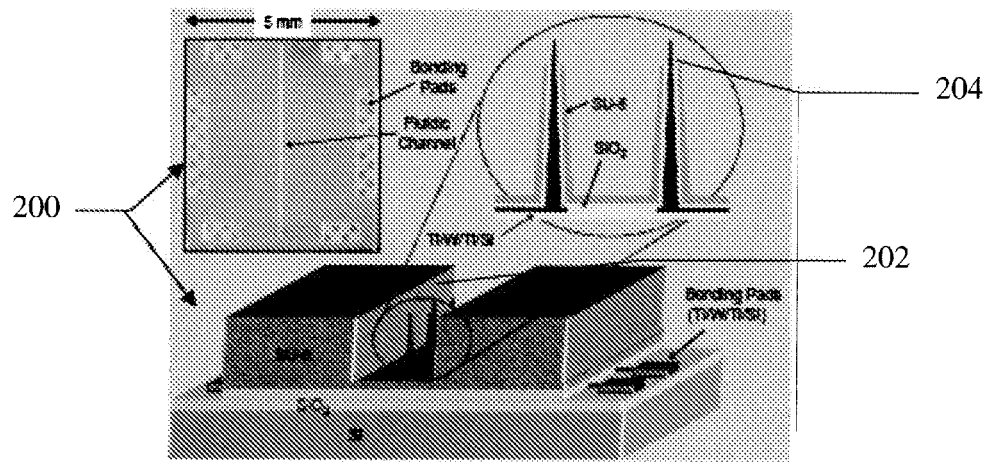
FIG. 40 is a schematic of a microfluidic device into which a plurality of carbon nanofibers are integrated into an array within a microfluidic channel of the device. This allows for the construction of multiscale devices capable of serial measurements. Individual nanofibers are electrically addressed using interconnect structures on the nanofiber substrate. Each nanofiber is passivated with an oxide layer, so that only the extreme tip is electrochemically active. Single fibers and nanofiber forest electrodes are configured. This exemplary figure was obtained from Dr. Timothy McKnight of Oak Ridge National Laboratory.

As illustrated in FIG. 40, the electrical circuitry can be formed on the SiO$_2$ substrate of a bulk silicon wafer using standard procedures. Thereafter, the carbon nanofiber array can be prepared such that each nanofiber is in electrical contact with the appropriate interconnect (see, e.g., Arumugam et al., "Wafer-scale fabrication of patterned carbon nanofiber nanoelectrode arrays: A route for development of multiplexed, ultrasensitive disposable biosensors," *Biosensors Bioelectronics* 24(9): 2818-2824 (2009); Melechko et al., "Vertically aligned carbon nanofibers and related structures: Controlled synthesis and directed assembly," *J. Appl. Phys.* 97(4):041301 (2005), each of which is hereby incorporated by reference in its entirety). Thereafter, SU-8 photoresist can be applied to the SiO$_2$ surface and the surface of the carbon nanofibers (with the exception of the very tip of each nanofiber) (Huang et al., "Microelectrode Arrays for Electrochemistry: Approaches to Fabrication," *Small* 5(7): 776-788 (2009); Potje-Kamloth et al., "Electrochemically Prepared Insulation for Carbon Fiber Microelectrodes," *Berichte der Bunsengesellschaft für Physikalische Chemie* 93(12):1480-1485 (1989), each of which is hereby incorporated by reference in its entirety). Finally, SU-8 material in bulk can be adhered to the applied SU-8 coating to form the microfluidic channel.

A further embodiment is a microfluidic sensor array that does not contain carbon nanofibers. This array includes (i) the one or more electrodes in communication with a microfluidic channel through which the fluid sample passes during the detection procedure. The one or more electrodes in each array can optionally be coated with the coating 108 described above in connection with sensor 100 (FIG. 29B). Regardless, the coated electrodes are positioned with their coating in communication with the microfluidic channel through which the fluid sample passes during the detection procedure.

Figure 37:
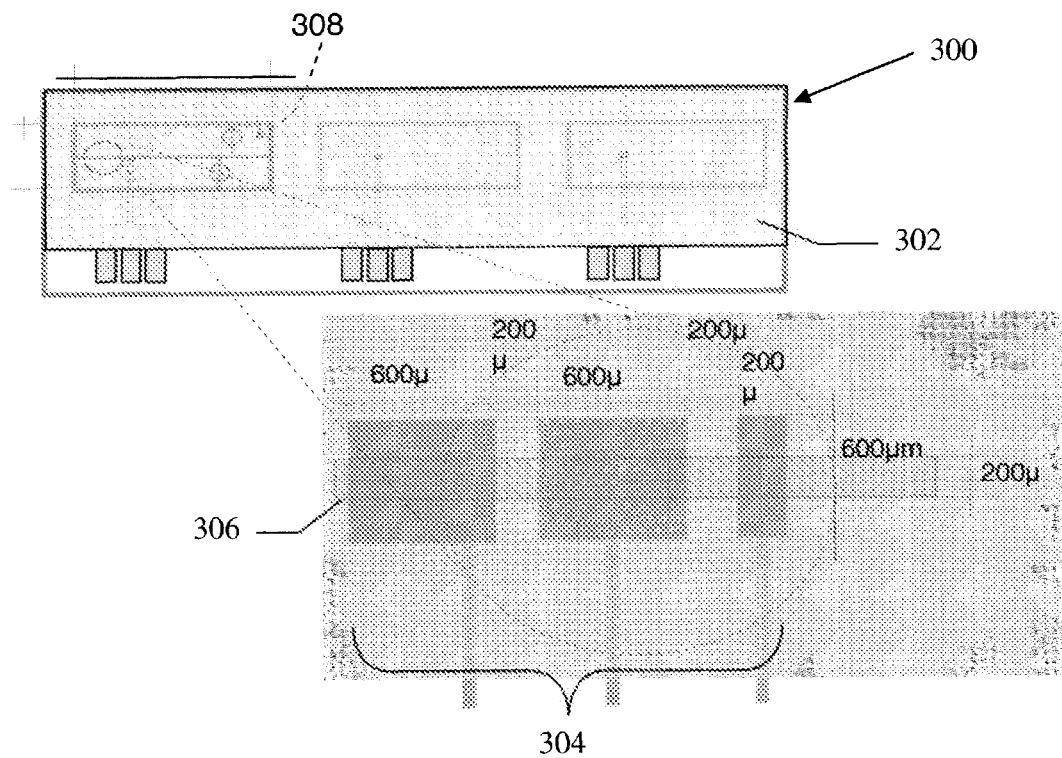
FIG. 37 is a plan view of a microfluidic DIPP biosensor with polyimide insulation and three microelectrochemical grid array sensors in series in a microfluidic channel. The electrochemical sensors are formed using 5 micron diameter gold discs positioned 50 µm center-to-center in a hexagonal arrangement.

In one embodiment, illustrated in FIG. 37, a microfluidic biosensor 300 is formed using a polyimide insulation 302 and three microelectrochemical grid array sensors 304 in series in a microfluidic channel 306 formed in a polydimethylsiloxane ("PDMS") block 308. Each array includes a reference electrode, counter electrode, and working electrode. The working electrodes are formed as microdisc arrays with 5 micron diameter gold discs positioned 50 µm center-to-center in a hexagonal arrangement. The channel 306 is provided with an inlet and outlet for moving the sample through the microchannel and across the sensor array.

Figure 38:
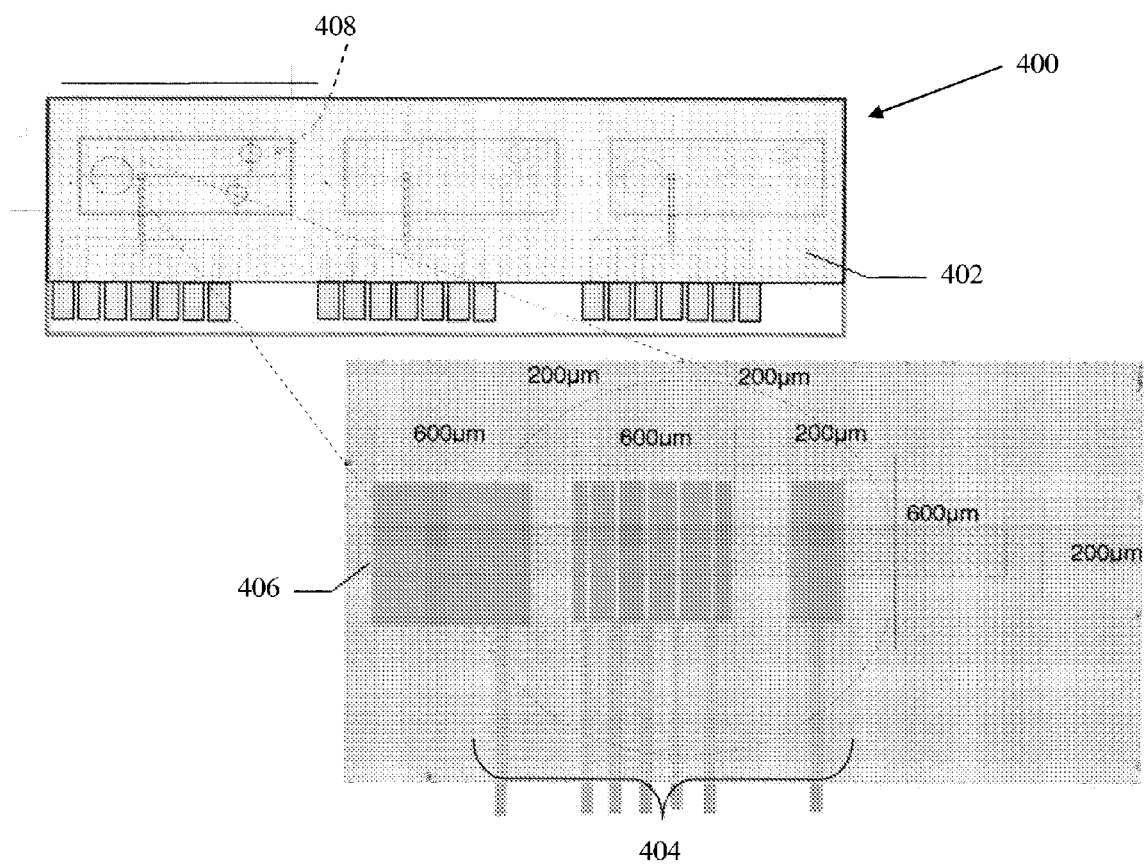
FIG. 38 is a plan view of a microfluidic DIPP biosensor with polyimide insulation and a microband sensor array in a microfluidic channel. 5 µm wide individually addressable bands are spaced 100 µm center-to-center. The sensors can optionally be interconnected with a single lead wire.

In another embodiment, illustrated in FIG. 38, a microfluidic biosensor 400 with polyimide insulation 402 utilizes individually addressable gold microband arrays (only the electrode at the center of 404) as working electrodes. The widths of the individual bands are between 2 and 10 microns. A complete biosensor 404 includes the microband array working electrode, reference electrode, and counter electrode in a microfluidic channel 406 formed in a PDMS block 408. The working electrodes is in the form of 5 µm wide individually addressable bands that are spaced 100 µm center-to-center. The sensors can optionally be interconnected with a single lead wire. The channel is provided with an inlet and outlet for moving the sample through the microchannel and across the sensor array.

Figure 39:
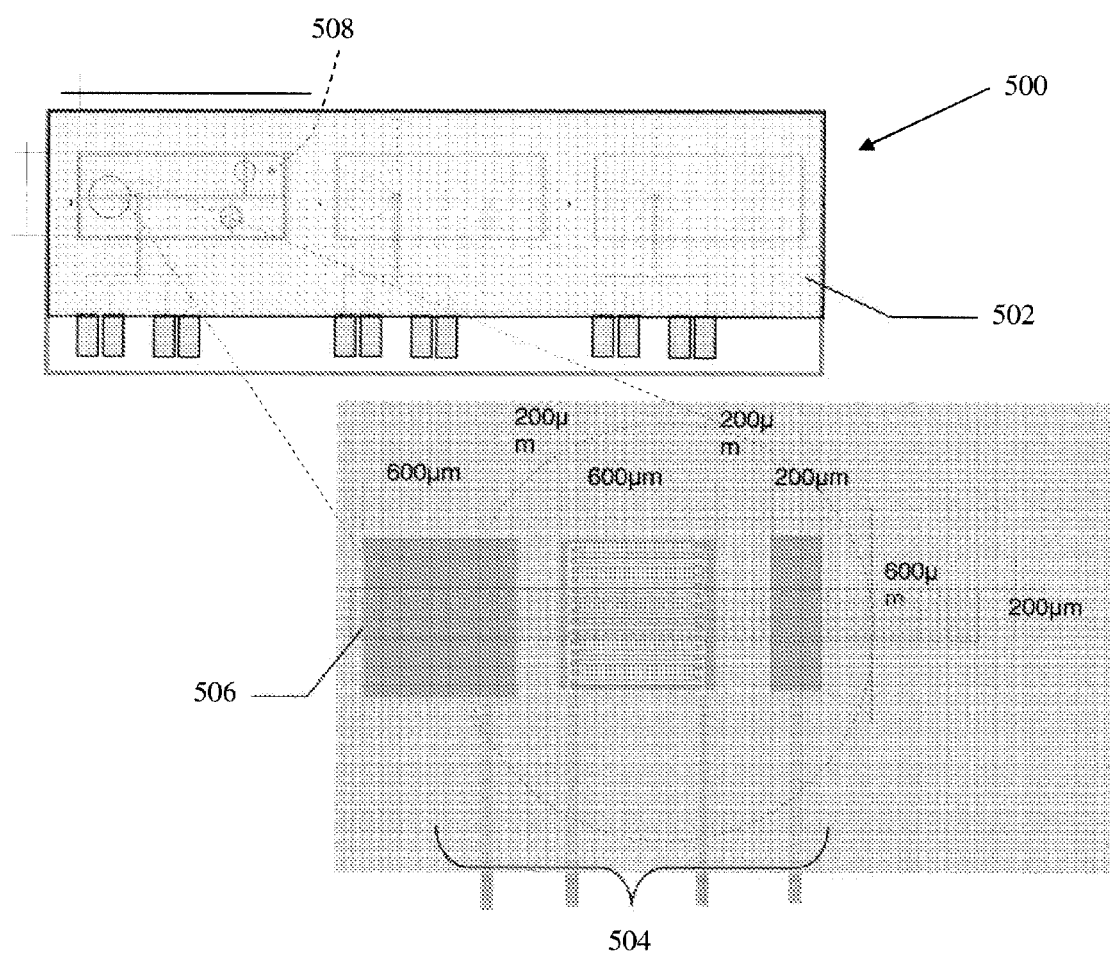
FIG. 39 is a plan view of a microfluidic DIPP biosensor with polyimide insulation and three interdigitated array electrochemical sensors in series in a microfluidic channel. The interdigitated electrode array includes with 5 µm wide fingers and 5 µm wide gaps between the fingers.

In a further embodiment, illustrated in FIG. 39, a microfluidic biosensor 500 is formed with polyimide insulation 502 and three interdigitated array 504 electrochemical sensors in series in a microfluidic channel 506 formed in a PDMS block 508. Each array includes a reference electrode, counter electrode, and working electrode. The working electrode is in the form of an interdigitated electrode array that includes 5 µm wide fingers and 5 µm wide gaps between the fingers. The channel is provided with an inlet and outlet for moving the sample through the microchannel and across the sensor array.

The embodiments illustrated in FIGS. 37-39 are exemplary, and the array electrodes can have varying dimensions ranging between, e.g., about 1 to 15 microns, preferably about 2 to 10 microns. The 2 micron disc arrays have been fabricated with 20 microns center to center distance, 5 micron disc arrays have been fabricated with 50 microns center to center distance, and 10 micron disc arrays have been fabricated with 100 microns center to center distance. The interdigitated electrodes have been fabricated with 2 microns, 5 microns and 10 micron fingers in combination with 2 microns, 5 microns and 10 micron gaps, respectively. Finally, individually addressable microband arrays have been fabricated with 2, 5 and 10 micron wide bands spaced 40, 100, and 200 microns apart.

Regardless of the array format, microfluidic devices are preferably fabricated from materials that are biocompatible and resistant to biofouling. Several existing materials, widely used for the fabrication of fluidic channels, can address these basic needs. Two categories can be distinguished among them: those based on glasses, such as glass, Pyrex, quartz, etc. (Ymeti et al., "Integration of Microfluidics with a Four-channel Integrated Optical Young Interferometer Immunosensor," *Biosens. Bioelectron.* 20:1417-1421 (2005), which is hereby incorporated by reference in its entirety); and those based on polymers such as polyimide, photoresist, SU-8 negative photoresist, PDMS, and silicone elastomer PDMS (McDonald et al., "Fabrication of Microfluidic Systems in poly(dimethylsiloxane)," *Electrophoresis* 21:27-40 (2000), which is hereby incorporated by reference in its entirety), liquid crystal polymer, Teflon, etc. While the glass materials have great chemical and mechanical resiliency, their high cost and delicate processing make them less frequently used for this kind of application. In contrast, polymers have gained wide acceptance as the materials of choice for fluidics applications. Moreover, structuring technologies involved in their use, such as bonding, molding, embossing, melt processing, and imprinting technologies, are now well developed (Mijatovic et al., "Technologies for Nanofluidic Systems: Top-down vs. Bottom-up—A Review," *Lab on a Chip* 5:492-500 (2005), which is hereby incorporated by reference in its entirety). An additional advantage of polymer-based microfluidic systems is that valves and pumps made with the same material are readily integrated (Unger et al., "Monolithic Microfabricated Valves and Pumps by Multilayer Soft Lithography," *Science* 288: 113-116 (2000), which is hereby incorporated by reference in its entirety).

PDMS and SU-8 resist are particularly well studied as raw materials for the construction of microfluidic systems. Their mechanical and chemical comportment are strongly disparate: SU-8 is stiffer (Blanco et al., "Microfluidic-optical Integrated CMOS Compatible Devices for Label-free Biochemical Sensing," *J Micromechanics Microengineering* 16:1006-1016 (2006), which is hereby incorporated by reference in its entirety) than PDMS, and so the structuring techniques of these two materials are different. PDMS is also subject to wall collapse, depending on the aspect ratios of the channels (Delamarche et al., "Stability of Molded poly-dimethylsiloxane," *Adv. Materials* 9:741-746 (1997), which is hereby incorporated by reference in its entirety). Their chemical properties are an important aspect for the wanted application. They both have a hydrophobic surface after polymerization, which can lead to an attachment of the proteins onto the PDMS walls, and can fill the channel in case of small cross-section. Both the surface of PDMS and of SU-8 can be treated with a surfactant or by plasma to become hydrophilic (Nordstrom et al., "Rendering SU-8 Hydrophilic to Facilitate use in Micro Channel Fabrication," *J Micromechanics Microengineering* 14:1614-1617 (2004), which is hereby incorporated by reference in its entirety). The composition of SU-8 can also be modified before its structuring to become hydrophilic after polymerization (Chen and Lee, "A Bonding Technique using Hydrophilic SU-8," *J Micromechanics Microengineering* 17:1978-1984 (2007), which is hereby incorporated by reference in its entirety). Fouling of the channel surface via nonspecific binding is an obvious concern for any microfluidic application. Anecdotal evidence suggests that SU-8 is less prone to this, but it is important to note that chemical treatment methods are also available for improving the performance of PDMS (Lee and Voros, "An Aqueous-based Surface Modification of poly(dimethylsiloxane) with poly(ethylene glycol) to Prevent Biofouling," *Langmuir* 21:11957-11962 (2004), which is hereby incorporated by reference in its entirety).

As noted above, the electrochemical sensor or sensor array is intended to be in contact with a fluid sample. As such, during use, the electrochemical sensor is intended to be exposed to a fluid sample. To facilitate exposure to the fluid sample, a fluid sample can be drawn from the patient and then exposed ex vivo to the sensor or sensor array. The sensor or sensor array according to any embodiment described herein is suitable for ex vivo detection of bioavailable drug concentration.

Alternatively, during use, the sensor or sensor array may reside in a device that is retained in fluid communication with the fluid sample in vivo. This type of device, because it is in constant exposure to the fluid sample during use, is preferably the electrochemical sensor having the coating over the electrodes as described above (which prevents biofouling of the working electrode during use) or a sensor array (containing a plurality of working electrodes) as described above.

Figure 41:
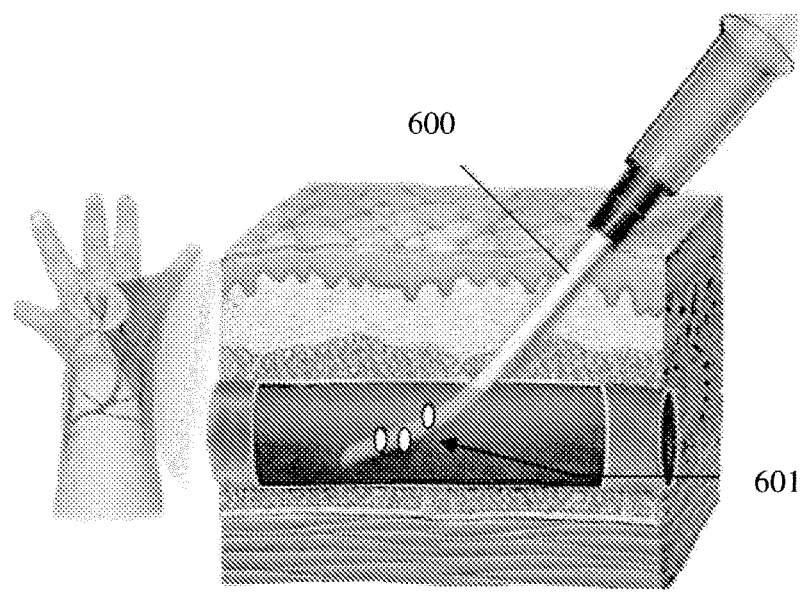
FIG. 41 is an illustration of a catheter of the invention that includes an electrochemical sensor of the present invention introduced into the body thereof, such that upon insertion of the catheter into a patient blood vessel, the electrochemical sensor is in fluid contact with the patient's blood for detection of bioavailable drug concentration.

One example of an in vivo device is a catheter of the type illustrated in FIG. 41. A catheter 600 includes a body and a lumen, and one or more electrochemical sensors 601 secured in the body with at least a portion of the sensor being in communication with either the lumen or externally of the body (such that the sensor(s) are exposed to the interior of a blood vessel). Preferably, the catheter 600 is an indwelling catheter. The catheter 600 can include a plurality of the electrochemical sensors 601 located at various positions along the body. During use, the catheter can be inserted into a blood vessel of a patient so that sensing of a bioavailable drug can be performed in vivo.

Other types of suitable catheters include, without limitation, indwelling solid fibers with electrochemical sensor(s), collinear catheters (that is, a cylinder or fiber inside another) equipped with electrochemical sensor(s), and catheters having different proximal and distal sensors.

Figure 42:
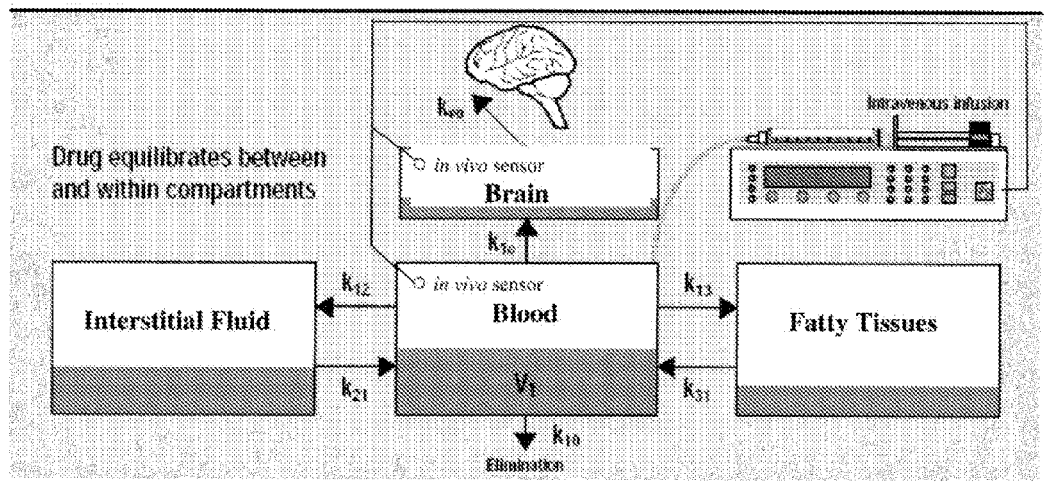
FIG. 42 is a schematic diagram illustrating the feedback mechanism for direct, real time feedback control by electrochemical biosensors regarding the bioavailable drug concentration. The measured bioavailable drug concentration is then used to direct drug delivery through a feedback loop to a pump.

The electrochemical sensor or sensor array of the present invention is particularly useful in combination with a target-controlled infusion drug delivery device. The design and construction of such drug delivery devices are well known in the art. The present invention involves modifying these known devices to include an electrochemical sensor or sensor array of the invention as a component in a feedback mechanism that is designed to control drug delivery (to the patient) based, at least in part, on the bioavailable drug concentration in a fluid sample from the patient (FIG. 42). Thus, rather than relying solely on pharmacodynamic models or physiological feedback mechanisms, the drug delivery device of the present invention also relies on the bioavailable drug concentration from the patient. As shown in FIG. 42, the bioavailable drug concentration can be detected in blood/lymph or cerebrospinal fluid.

Exemplary drug delivery devices that can be modified include those described in U.S. Pat. No. 7,220,240 to Struys et al., U.S. Patent Publ. Nos. 2007/0118075 to Kimmo et al. and 2006/0167722 to Struys et al., J. Glen et al., "The Development of 'Diprifusof': A TCI System for Propofol," Anesthesia, 53, Supplement 1, pp. 13-21 (1998); J. Gray et al., "Development of the Technology for 'Diprifusof' TCI Systems," Anesthesia, 53, Suppl. 1, pp. 22-27 (1998), each of which is hereby incorporated by reference in its entirety.

Figure 43:
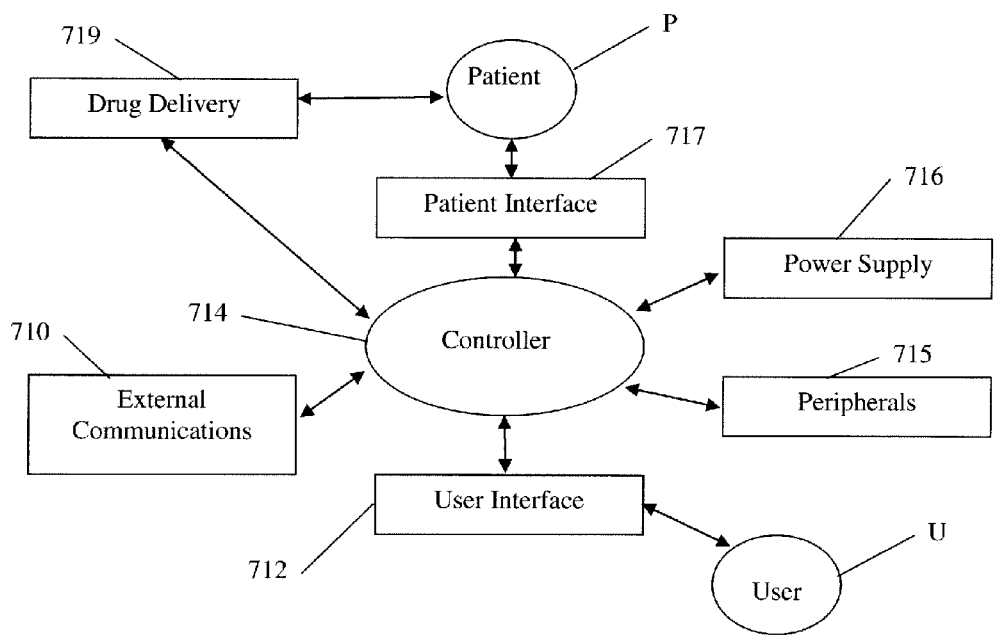
FIG. 43 is a block diagram illustrating a drug delivery system suitable for delivering sedation or analgesic drugs. The drug delivery system is integrated with an electrochemical sensor of the present invention to regulate drug delivery directly.

With reference to FIG. 43, a block diagram depicting one embodiment of a drug delivery system 700 that is equipped with an electrochemical sensor of the invention is illustrated. The system 700 includes user interface 712, software controlled controller 714, peripherals 715, power supply 716, external communications 710, patient interface 717, and drug delivery 719, where sedation and analgesia system 700 is operated by user U to provide drug delivery (e.g., sedation and/or analgesia) to patient P. The basic structure of this sedation and analgesia system 700 is disclosed by U.S. Pat. No. 6,745,764 to Hickle, which is hereby incorporated by reference in its entirety; but the system is modified such that the patient interface 717 includes an electrochemical sensor of the present invention.

Briefly, the drug delivery 719 includes a drug reservoir (which preferably, during use, includes an electrochemically active drug of the type described above), and a pump in communication with the drug reservoir.

The patient interface 717 includes an electrochemical sensor or sensor array of the present invention, which produces an output current from a reduction-oxidation (redox) reaction at electrochemical sensor in the presence of the bioavailable drug. As noted above, the electrochemical sensor or sensor array of the present invention can be located ex vivo or in vivo. Regardless of its position with respect to the patient, the amount of output current produced is in direct correlation to an amount of bioavailable drug detected during a measuring event (i.e., within a patient fluid sample). The output current from electrochemical sensor is coupled to a current/voltage detector which can be configured to convert the detected current output from electrochemical sensor into a corresponding calibrated value.

Using the sensor or sensor array of the present invention in combination with fluid samples containing known concentrations of a bioavailable form of a drug, it is possible to generate empirical data that correlates the detected conditioned current/voltage levels with the bioavailable drug concentration. This empirical data can be used to form a model, which can be stored in memory.

The controller 714 can include an input/output (I/O) card coupled through a data bus into a processor. The conditioned current at the output of current/voltage detector is provided to an analog to digital converter (ADC) inside controller 714. The ADC converts the analog output of current/voltage detector to a corresponding digital value for processing by controller 714. The digital value of the detected current is provided to central processing unit (CPU)/processor via an internal bus. By way of example only, the ADC can be an 8-bit ADC, although other types of ADCs may also be used as known to those skilled in the art.

CPU/processor receives and processes the digital current from ADC. CPU/processor can be in the form of a single board computer which includes one or more microprocessors or CPUs. Controller 714 may be conveniently implemented using one or more general purpose computer systems, microprocessors, digital signal processors, and microcontrollers, programmed according to the teachings described and illustrated herein. For example, CPU/processor can be an Intel Core Duo® processor provided by Intel Corporation of Santa Clara, Calif. Alternatively, CPU/processor may be a special purpose processor designed and fabricated to carry out various aspects of this invention. For example, CPU/processor may be an application specific integrated circuit (ASIC) chip.

Figure 44:
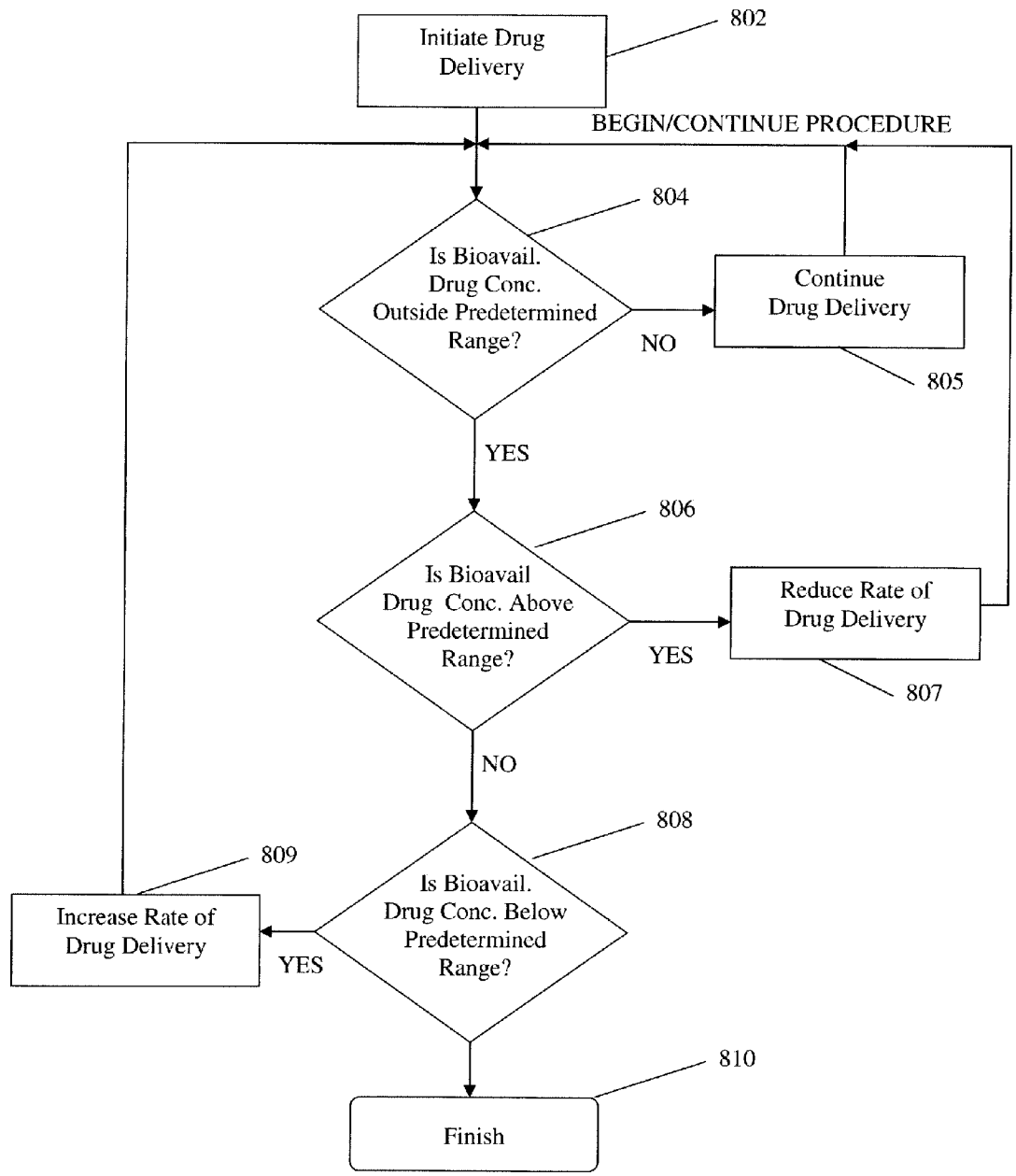
FIG. 44 is a flow chart of a method for detecting bioavailable drug concentration, i.e., in a patient, and then regulating the delivery rate of the drug to the patient in accordance with various aspects of this invention.

CPU/processor is coupled to a memory that stores various settings for the delivery system 700. For example, memory stores one or more threshold values of the output current from electrochemical sensor, which threshold values represent the target range for the bioavailable drug concentration, i.e., minimum and maximum bioavailable drug concentrations. The memory can be a random access memory (RAM) and/or read only memory (ROM), along with other conventional integrated circuits used on a single board computer as are well known to those of ordinary skill in the art. Alternatively or in addition, the memory may include a floppy disk, a hard disk, CD ROM, or other computer readable medium which is read from and/or written to by a magnetic, optical, or other reading and/or writing system that is coupled to one or more processors. The memory can include instructions written in a computer programming language or software package for carrying out one or more aspects of the present invention as described and illustrated herein, although some or all of the programmed instructions could be stored and/or executed elsewhere. For example, instructions for executing steps outlined in FIG. 44 can be stored in a distributed storage environment where memory is shared between one or more controllers similar to controller 714.

Controller 714 can include an input/output (I/O) device (e.g., an I/O card) coupled to CPU/processor. The user interface 714 (e.g., display with keypad), external communications 710, peripherals 715, patient interface 717, and drug delivery 719 can be coupled to the controller 714 via and internal bus. The I/O device includes a bi-directional port for communication to/from other computing and/or electronic devices via a link. The port can also be used for charging the device via power supply 716, which can be a battery. By way of example only, the port can be a Universal Synchronous Bus (USB) port, although other types of communication and input/output ports may also be used, as known to those skilled in the art.

The internal bus is designed to carry data, power and ground signals, as known to one skilled in the art. By way of example only, internal bus can be a Peripheral Component Interconnect (PCI) bus, although other types of local buses (e.g., Small Computer System Interface or "SCSI") may also be used, as known to those skilled in the art.

User interface 712 can be a suitable display panel on which instructions and data are presented to a user in both textual and graphic format. In addition, display 712 can include a touch screen also coupled to the I/O device for accepting input from a user (e.g., a medical professional). The display can display the concentration of the bioavailable drug concentration based on the output current or voltage that is generated by the electrochemical sensor. Further, the display can be substituted by or used in conjunction with an audio device (e.g., a speaker, a buzzer, or a beeper alarm) controlled by CPU/processor to indicate whether the bioavailable drug concentration is too high or too low.

The controller 714 receives power from a power supply 716. Power supply 716 can be a battery or a direct pluggable outlet to a main power-line. Alternatively, power supply 716 may be a switched mode power supply (SMPS) commonly used in computer systems, although other forms for powering controller 714 using power supply may also be used, as known to those skilled in the art.

The controller 714 preferably carries out a PID controller algorithm using the input from the electrochemical sensor. The PID controller involves three separate parameters: the Proportional, the Integral and Derivative values. The Proportional value determines the reaction to the sensed bioavailable drug concentration, the Integral value determines the reaction based on the average bioavailable drug concentration, and the Derivative value determines the reaction to the rate at which the bioavailable drug concentration has been changing. In the context of the present invention, any one of these parameters or the weighted sum of any two (or all three) of these parameters can be used to adjust the rate of drug discharge by the drug delivery 719.

From the foregoing, it should be appreciated that the present invention also relates to a method for electrochemical detection of bioavailable drug concentration in a fluid sample, which includes the steps of: exposing a fluid sample to an electrochemical sensor comprising one or more electrodes and a coating that surrounds the one or more electrodes, which coating is capable of partitioning the bioavailable drug directly from the fluid sample; and detecting an oxidation/reduction current during said exposing, wherein the detected current relates to the concentration of bioavailable drug in the fluid sample.

The present invention also relates to a method of modulating drug delivery that includes the steps of: exposing a fluid sample obtained from a patient to an electrochemical sensor or sensor array of the present invention, the electrochemical sensor capable of detecting a bioavailable drug concentration in a fluid sample; detecting an oxidation/reduction current during said exposing, wherein the detected current relates to a concentration of bioavailable drug in the fluid sample; then modulating delivery of the drug into a patient based on the concentration of the bioavailable drug in the fluid sample.

Because the patient receiving the drug is monitored continuously during the procedure for which the drug is being administered, the detection of bioavailable drug concentration is preferably performed repeatedly during a surgical procedure such that appropriate feedback control is provided to maintain the bioavailable drug concentration within an optimal range. While the frequency of the detection step can vary depending on the pharmacokinetics of a particular drug, it is generally desirable to repeat the detection procedure at least every 5 minutes, more preferably at least every 2 to 3 minutes. More frequent detection procedures can also be carried out.

As a consequence of the frequent monitoring of bioavailable drug concentration, the output from the electrochemical sensor can be used to modify operation of the drug pump in real time (as noted above). Preferably, adjustments in drug delivery, if any, are made instantaneously following the detection event (i.e., within the capacity of the processor control system). The method of modulating drug delivery can include the embodiment illustrated in FIG. 44. Upon initiation of drug delivery at step 802, either via bolus or predetermined delivery rate, drug delivery begins. This step may occur at a predetermined time prior to surgery. Prior to beginning the surgical procedure and periodically during the course of the surgical procedure, the query at step 804 initiates measurement of the bioavailable drug concentration using the electrochemical sensor of the present invention. If the bioavailable drug concentration remains with the predetermined range (e.g., about 3 to about 8 µg/ml for Propofol as an anesthetic, or about 1 to about 2 µg/ml for Propofol as a sedative), then at step 806 the existing drug delivery rate is maintained. (If this is the first measurement with the bioavailable drug concentration within the target range, the surgical procedure can begin at this time.) If the bioavailable drug concentration is outside the predetermined range, then the output of the electrochemical sensor is assessed at steps 806 and 808, respectively, to determine whether the detected bioavailable drug concentration is above or below the predetermined range. If the bioavailable drug concentration detected during a single detection step is above an acceptable range, then the rate of drug delivery can be reduced or entirely withdrawn for a short duration at step 807. A reduction can be automated via the PID controller. If the bioavailable drug concentration detected during a single detection step falls below an acceptable range, then an immediate change in the rate of drug delivery can be made, a single bolus can be administered, or both, at step 809. An increase can be automated via the PID controller. These steps can be carried out using a suitable software algorithm, and they can be repeated at periodic intervals during the surgical procedure. Upon completion of the surgical procedure, the drug delivery protocol can be withdrawn at step 810.

As is known in the art, the software algorithm (PID controller) used to adjust drug delivery rate can also rely on one or more patient physiological response parameters, including blood pressure, heart rate, temperature, and EEG parameters. See Wang et al., "New Target Controlled Infusion Using a Hybrid Physiology Based Pharmacokinetic Model," *IEEE* 1822-1824 (2008) (ISBN: 978-1-4244-1747-6), which is hereby incorporated by reference in its entirety. In addition to the foregoing, it should be appreciated by persons of skill in the art that drug administration is not limited to surgical procedures, but can also be effectively used in other settings, e.g., during intensive care or post-operative care.

EXAMPLES

The Examples set forth below are for illustrative purposes only and are not intended to limit, in any way, the scope of the present invention.

Example 1—Macroelectrode Design and Use for Propofol Detection 2,6-Diisopropylphenol (Propofol, DIPP) was purchased from Aldrich (D126608, St. Louis, Mo.) and used as received for preparation of stock solution 0.01M in 0.1 M NaOH or 0.1M in 3:7 mixture of water to methanol. All other aqueous solutions were prepared with Milli-Q Gradient A10 purified water.

Voltammetric measurements were performed using the Autolab/PGSTAT12 system equipped with the GPES Version 4.8 (Eco Chemie, Urtrecht, NL) in a standard three-electrode cell setup, i.e., with the platinum (2 mm diam.) or glassy carbon (BAS, 3 mm d.) disks macroelectrodes serving as working electrodes and the double junction (with 10% $KNO_3$) Ag/AgCl Model 90-02 (Orion Research, Beverly, Mass.) and Pt-wire as reference and counter electrodes, respectively. Working macroelectrodes were always polished (using 0.3 µm particle size alumina) prior to use. The carbon microelectrodes were manufactured by standard lithography methods (Guillorn et al., "Individually Addressable Vertically Aligned Carbon Nanofiber-based Electrochemical Probes," *J. Appl. Phys.* 91:3824 (2002), which is hereby incorporated by reference in its entirety).

Cyclic voltammetry on a platinum working electrode in the potential range of −0.3 to 1.4V in $10^{-2}$M $H_2SO_4$ did not demonstrate an electrochemical signal for DIPP at concentrations up to $4 \times 10^{-4}$M. Rather, the significant oxidation current signal seen only marks the electrode passivation in platinum oxide region, where observed. Voltammetry in the potential range of −0.7 to 1V in $10^{-2}$M NaOH also failed to demonstrate a signal for the same concentration of DIPP.

Conversely, cyclic voltammetry on a glassy carbon electrode in the potential range of −0.5 to 1.2V in $10^{-2}$M $H_2SO_4$ for a concentration of $10^{-4}$M DIPP demonstrated an increasing current signal with repeated cycles (FIG. 1). Starting the cycling at 0.2V in the positive potential direction, the first oxidation mark in shape of current peak was observed at around 0.7V. On the negative scan, there appeared two reduction peaks at the start of cycling, which grew with continual cycling and merged later into one with peak potential around 0V. On the positive scan direction, the growth of an additional oxidation peak at 0.4V was observed. The latter two growing peaks may be attributed to the development of an electrochemically active biofilm layer on carbon surface with the peak at 0.7V growing apparently at much slower rate. The slightly positive shifted can be correlated exclusively with direct DIPP oxidation—slower growth reflecting most likely an increase of effective electrode surface.

Figure 2:
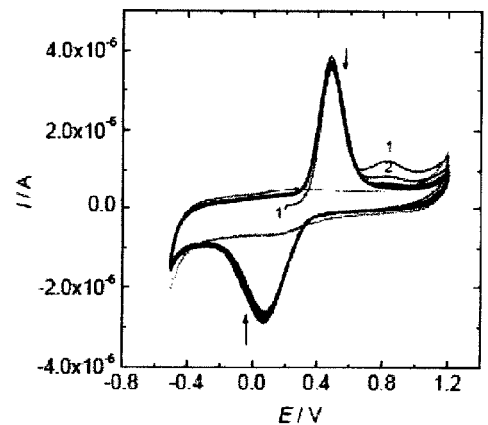
FIG. 2 is a cyclic voltammogram of $10^{-2}$M $H_2SO_4$ only, using 100 mV/s scan, 10 cycles; this was carried out after 10 cycles following DIPP introduction. Working electrode=glassy carbon; counter electrode=Pt; and reference electrode=Ag/AgCl. The DIPP peak disappeared by the third cycle shown.

These statements can be supported by voltammetry of developed layer in background electrolyte in the absence of DIPP (FIG. 2). As can be seen, with continuous cycling, only two peaks corresponding to the electrochemically active layer remained and the direct oxidation peak of DIPP rapidly disappeared after oxidation of adsorbed traces of (see $3^{rd}$ cycle, FIG. 2). The overall reaction resulting in the electrochemically active layer (FIG. 2 arrow, biofilm) formed on the surface of the glassy carbon electrode is of uncertain origin.

Figure 3:
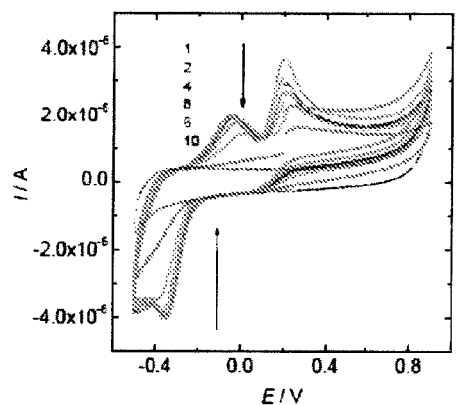
FIG. 3 is a cyclic voltammogram of $2 \times 10^{-4}$M DIPP in $10^{-2}$M NaOH using 100 mV/s scan, 10 cycles. The DIPP was introduced from a 0.01M solution in 0.1M NaOH water. Working electrode=glassy carbon; counter electrode=Pt; and reference electrode=Ag/AgCl.
Figure 4:
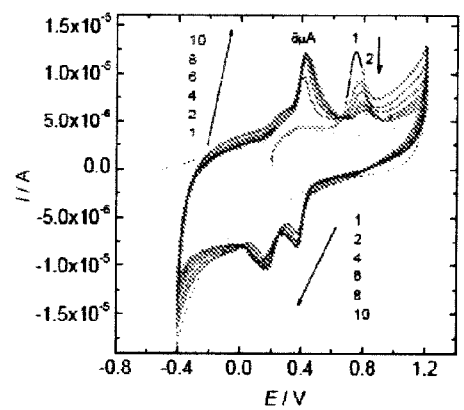
FIG. 4 is a cyclic voltammogram of $10^{-4}$M DIPP in $10^{-2}$M $H_2SO_4$ using 100 mV/s scan, 10 cycles. The DIPP was introduced from a 0.1M solution in methanol. Working electrode=glassy carbon; counter electrode=Pt; and reference electrode=Ag/AgCl.

Similar EC behavior can be expected from a polymerized conducting polymer layer or from deposited and still electrochemically active but insoluble DIPP oxidation product. A roughly similar shape of voltammogram was obtained in $10^{-2}$M NaOH (−0.5 to 0.9V), but with significant difference, all developed peaks decreased with continuous cycling (FIG. 3). The minimally active formed passivation layer when further cycled in $10^{-2}$M NaOH disappeared immediately after immersion into solution, thus showing its high solubility. The consequences that follow from these observations therefore suggest the importance of protons in overall reaction scheme and demonstrate that analysis in acidic media is required. It's also noteworthy the effect of methanol in stock solution on the shape and rate of the growing current. FIGS. 1-3 depict curves measured without presence of methanol in sample. Same experiment in FIG. 1 was performed with methanol in the sample solution and is shown in FIG. 4. The differences in the curves, including those obtained for background electrolytes are hypothesized to result from methanol co-adsorption on carbon surface.

Figure 5:
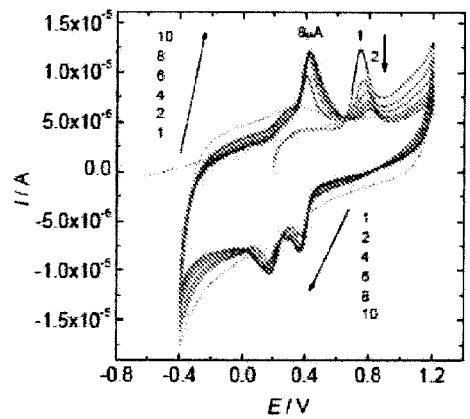
FIG. 5 is a cyclic voltammogram of $10^{-4}$M DIPP in $10^{-1}$M $H_2SO_4$ using 100 mV/s scan, 10 cycles. The DIPP was introduced from a 0.1M solution in methanol. Working electrode=glassy carbon; counter electrode=Pt; and reference electrode=Ag/AgCl.
Figure 6:
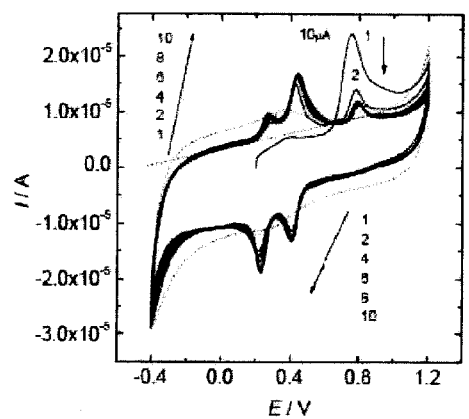
FIG. 6 is a cyclic voltammogram of $10^{-4}$M DIPP in 1M $H_2SO_4$ using 100 mV/s scan, 10 cycles. The DIPP was introduced from a 0.1M solution in methanol. Working electrode=glassy carbon; counter electrode=Pt; and reference electrode=Ag/AgCl.
Figure 7:
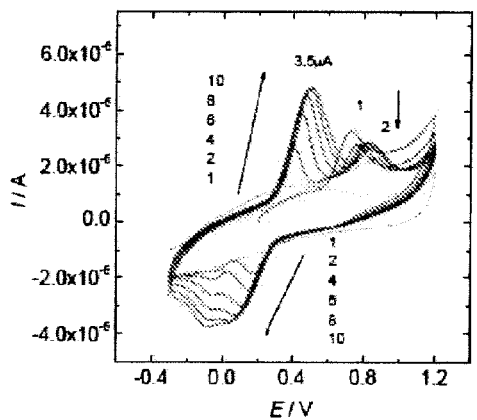
FIG. 7 is a cyclic voltammogram of $10^{-4}$M DIPP in $10^{-3}$M $H_2SO_4$ using 100 mV/s scan, 10 cycles. The DIPP was introduced from a 0.01M solution in 0.1M NaOH water. Working electrode=glassy carbon; counter electrode=Pt; and reference electrode=Ag/AgCl.

The concentration effects of the $H_2SO_4$ solute in presence of methanol are shown in FIGS. 5-6. The greater the concentration of $H_2SO_4$ in solution, the sooner the non-growing stable shape of curves is reached.

Figure 8:
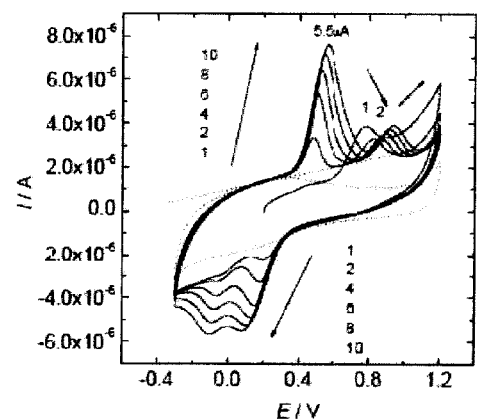
FIG. 8 is a cyclic voltammogram of $10^{-4}$M DIPP in $10^{-2}$M $H_2SO_4$ using 100 mV/s scan, 10 cycles. The DIPP was introduced from a 0.01M solution in 0.1M NaOH water. Working electrode=glassy carbon; counter electrode=Pt; and reference electrode=Ag/AgCl.
Figure 9:
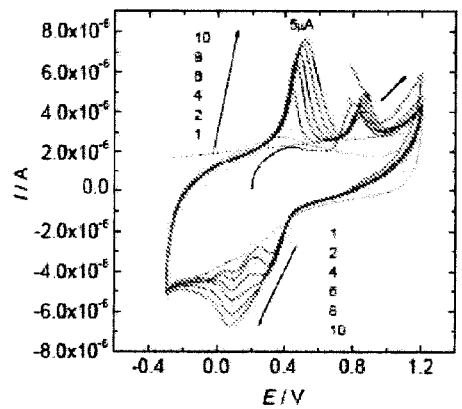
FIG. 9 is a cyclic voltammogram of $10^{-4}$M DIPP in $10^{-1}$M $H_2SO_4$ using 100 mV/s scan, 10 cycles. The DIPP was introduced from a 0.01M solution in 0.1M NaOH water. Working electrode=glassy carbon; counter electrode=Pt; and reference electrode=Ag/AgCl.
Figure 10:
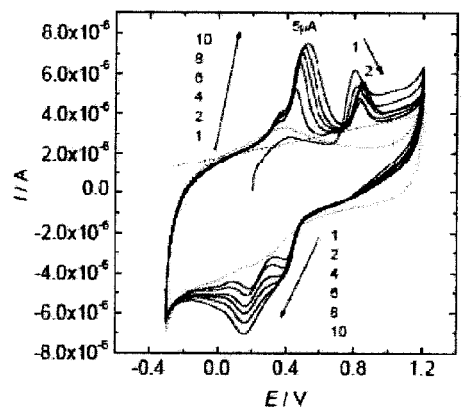
FIG. 10 is a cyclic voltammogram of $10^{-4}$M DIPP in 1M $H_2SO_4$ using 100 mV/s scan, 10 cycles. The DIPP was introduced from a 0.01M solution in 0.1M NaOH water. Working electrode=glassy carbon; counter electrode=Pt; and reference electrode=Ag/AgCl.

Similar pH dependence with aqueous samples is presented in FIGS. 7-10. These show maximum peak currents and the greatest growth at a concentration of $10^{-2}$ M $H_2SO_4$ (FIG. 8 replicates the experiment in FIG. 1). Higher concentrations of protons in the solution do not increase the signal intensity or current peak height. Rather, there is an increase in the system noise demonstrated by the broadening of the redox curves in FIGS. 9-10.

Figure 11:
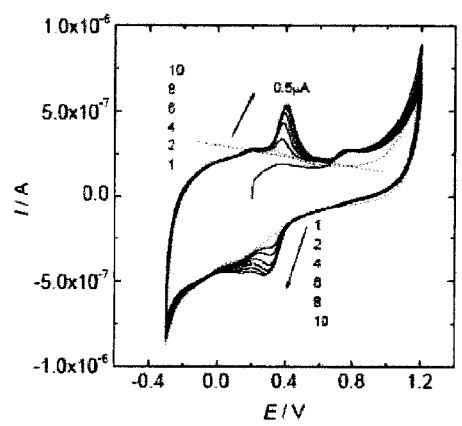
FIG. 11 is a cyclic voltammogram of $10^{-5}$M DIPP in $10^{-2}$M $H_2SO_4$ using 10 mV/s scan, 10 cycles. The DIPP was introduced from a 0.01M solution in 0.1M NaOH water. Working electrode=glassy carbon; counter electrode=Pt; and reference electrode=Ag/AgCl.
Figure 12:
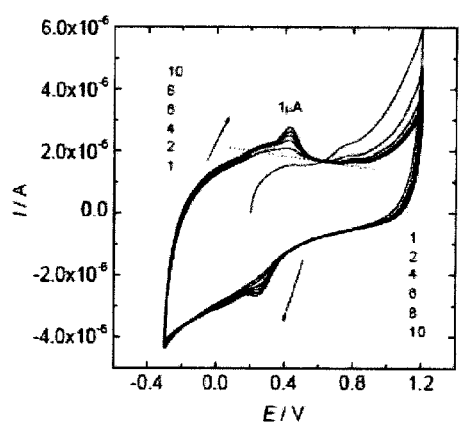
FIG. 12 is a cyclic voltammogram of $10^{-5}$M DIPP in $10^{-2}$M $H_2SO_4$ using 100 mV/s scan, 10 cycles. The DIPP was introduced from a 0.01M solution in 0.1M NaOH water. Working electrode=glassy carbon; counter electrode=Pt; and reference electrode=Ag/AgCl.

The potential effects of the cycling rate on the DIPP signal were examined in FIGS. 11-12. These show the effects of different voltage cycling scan rates on the growing DIPP signal peaks at lower concentrations, e.g. $10^{-5}$M DIPP. A slower cycling rate generates a larger signal peak in identical solutions, indicating that the sensitivity of the DIPP signal can be optimized by the voltammetry method used (see also FIG. 23, infra). Importantly, the concentration of DIPP used in this set of experiments is in the therapeutic range of clinical use.

Figure 13:
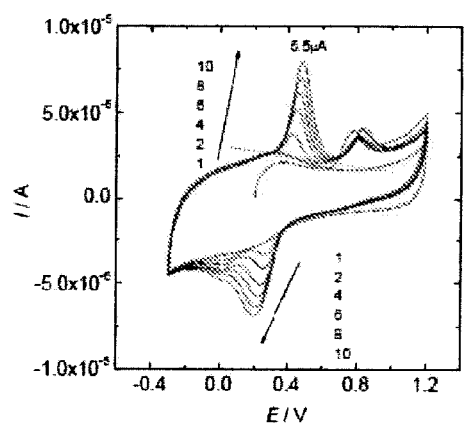
FIG. 13 is a cyclic voltammogram of $10^{-4}$M DIPP in $10^{-2}$M $H_2SO_4$+0.05% Tween20 using 100 mV/s scan, 10 cycles. The DIPP was introduced from a 0.01M solution in 0.1M NaOH water. Working electrode=glassy carbon; counter electrode=Pt; and reference electrode=Ag/AgCl.
Figure 14:
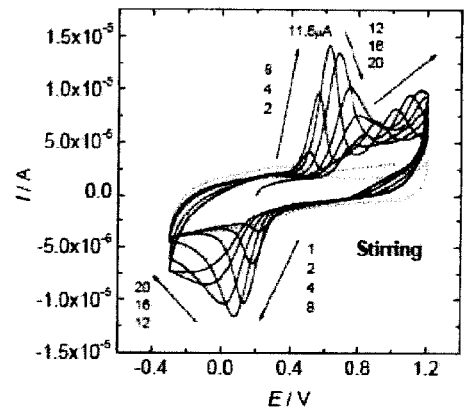
FIG. 14 is a cyclic voltammogram of $10^{-4}$M DIPP in $10^{-2}$M $H_2SO_4$+0.05% Tween20 using 100 mV/s scan, 20 cycles with stirring. The DIPP was introduced from a 0.01M solution in 0.1M NaOH water. Working electrode=glassy carbon; counter electrode=Pt; and reference electrode=Ag/AgCl.

Some of the biophysical characteristics of the DIPP biofilm were investigated using a series of studies to determine whether the DIPP signal could be modified or enhanced by the presence of various detergents in the solution (FIGS. 13-14). These studies depict the effect of the surfactant Tween-20 on the regularity of surface layer growth and the additional effects on growth by stirring of the solution.

Figure 15:
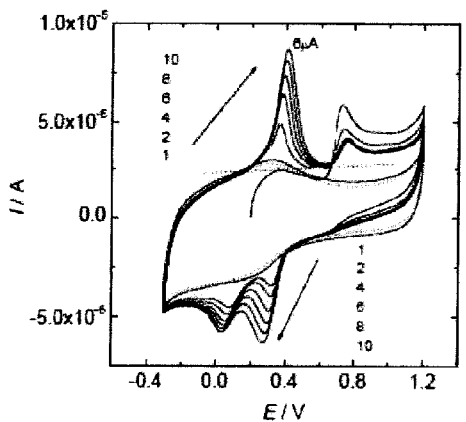
FIG. 15 is a cyclic voltammogram of $10^{-4}$M DIPP in $10^{-2}$M $H_2SO_4$+$10^{-3}$M sodium lauryl sulfate using 100 mV/s scan, 10 cycles. The DIPP was introduced from a 0.01M solution in 0.1M NaOH water. Working electrode=glassy carbon; counter electrode=Pt; and reference electrode=Ag/AgCl.
Figure 16:
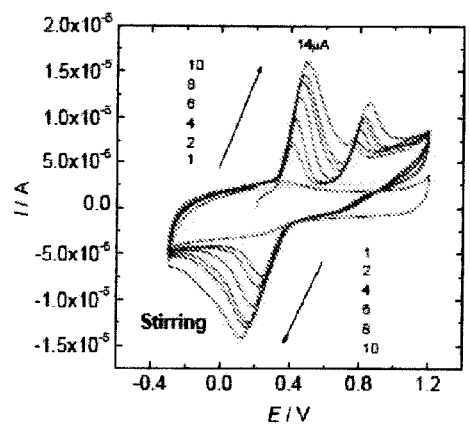
FIG. 16 is a cyclic voltammogram of $10^{-4}$M DIPP in $10^{-2}$M $H_2SO_4$+$10^{-3}$M sodium lauryl sulfate using 100 mV/s scan, 10 cycles with stirring. The DIPP was introduced from a 0.01M solution in 0.1M NaOH water. Working electrode=glassy carbon; counter electrode=Pt; and reference electrode=Ag/AgCl.

Similar studies were performed using $10^{-3}$M sodium lauryl sulfate (SDS detergent) and are shown in FIGS. 15-16. These studies show an increasing DIPP signal in the presence of SDS both with and without stirring of the solution. This was evident both in the accumulation times and stripping current peak with or without SDS.

The studies in FIGS. 17-18 also clearly demonstrate that the maximal EC signal is obtained within 30 seconds when the solution is stirred in the presence of SDS. Stirring alone does not optimize the signal acquisition as is shown in FIG. 18. Here, the maximal signal was not been reached even after 200 seconds in the absence of SDS in the solution. Thus, the presence of SDS detergent is important (but not critical, see FIG. 19, below) for the rapid determination of the DIPP electrochemical signal.

The studies in FIGS. 19-20 demonstrate that the DIPP signal is clearly concentration dependent (accumulation time 50 s) even in the absence of SDS for concentrations of DIPP $>1\times10^{-5}$M. The signal intensity (current) is increased in the presence of SDS, thus enhancing the potential to more accurately quantify the level of the drug in the presence of SDS detergent.

The relationship between the SDS concentration and the DIPP signal intensity is shown in FIG. 21. The optimal SDS concentration which maximizes the DIPP signal under stirring conditions is $10^{-3}$M (1 mM). Under these conditions, a robust DIPP signal is seen at concentrations above $3\times10^{-5}$M (FIG. 22). Finally FIG. 23 shows the relationship between the charge under the DIPP stripping peak and the voltage scan rate. See also FIGS. 11-12 supra.

Example 2—Microelectrode Design and Use for Propofol Detection

Figure 24:
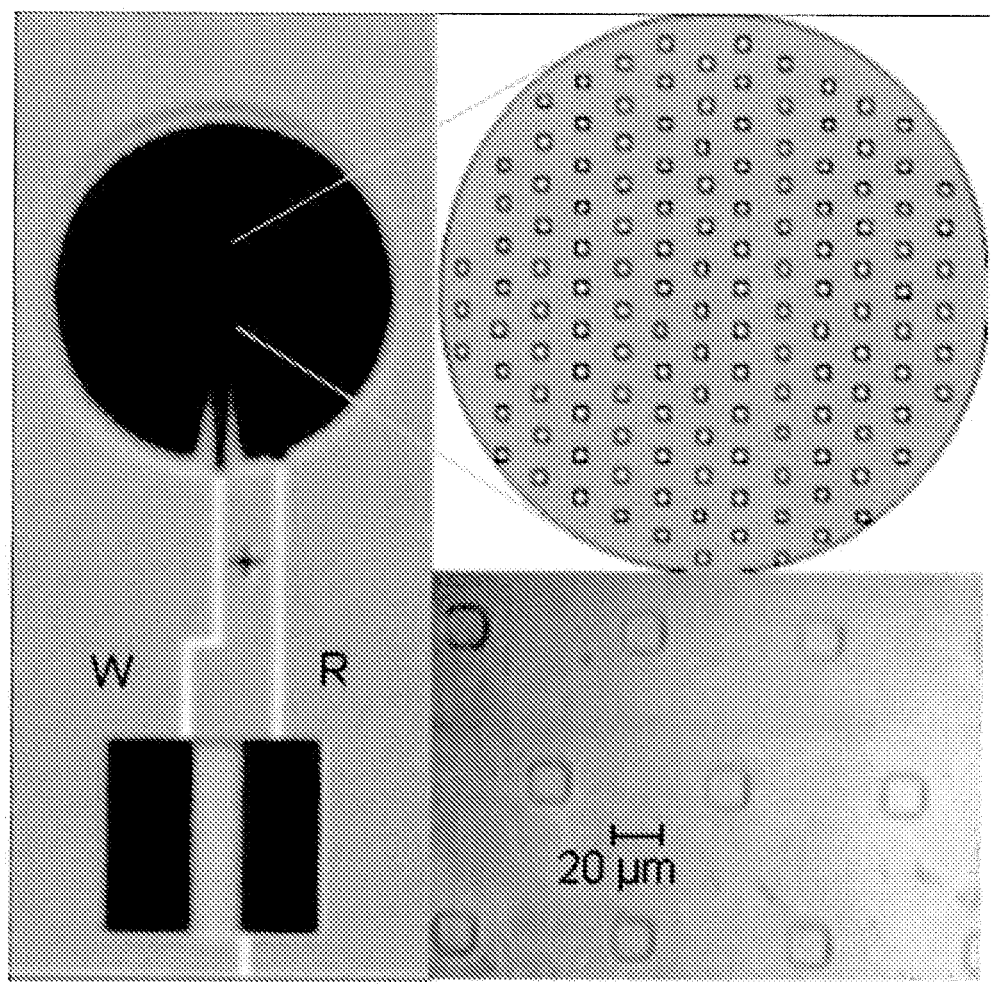
FIG. 24 is a microscopic image a fabricated carbon microelectrode containing a grid array of electrochemical sensors.

To develop a simple and faster "in-line" analytical technique for small sample volumes, the glassy carbon macroelectrode of Example 1 was replaced by a carbon microelectrode having the structure illustrated in FIG. 24.

The carbon microelectrode was prepared by the Oak Ridge National Laboratory using microfabrication technologies as previously described in the literature, (Guillorn et al., "Individually Addressable Vertically Aligned Carbon Nanofiber-based Electrochemical Probes," *J. Appl. Phys.* 91: 3824 (2002); McKnight et al., "Effects of Microfabrication Processing on the Electrochemistry of Carbon Nanofiber Electrodes," *J Phys Chem B* 107(39):10722-10728 (2003), each of which is hereby incorporated by reference in its entirety).

Figure 25:
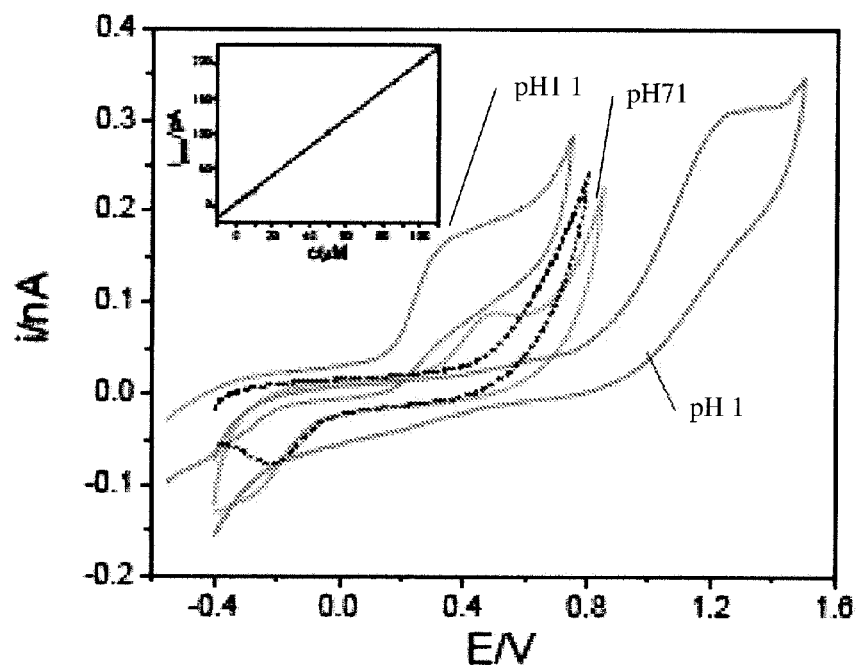
FIG. 25 is an overlay of cyclic voltammograms of the Propofol signal using carbon microelectrodes at varying pH values. Blue curve, pH1; neutral pH7 (dashed line 1st cycle, red line 2nd cycle), and green curve, pH11. Calibration curve (inset) is measured at pH7 and demonstrates a linear, dose-dependent response.

Having fabricated the carbon microelectrode, additional experiments were performed to the include a broad pH range (acidic, neutral, and basic solutions). These results are illustrated in FIG. 25. FIG. 25 shows cyclic voltammograms of Propofol using a 25-μm-diameter carbon microelectrode obtained in acidic (pH1, blue curve), physiologic (pH7; dashed line for 1st cycle, red line for 2nd cycle), and alkaline (pH11, green curve) solutions.

The steady-state current of oxidized Propofol measured in acidic solution is two times greater than in alkaline solution (FIG. 25, ~1.8 vs. ~3.5 i/nA). This implies that the mechanism of electrochemical oxidation of Propofol is different between acidic and alkaline solutions. Either i) the number of electrons involved in the electrode reaction at acidic pH is twice the number of electrons involved at alkaline pH, or ii) there are two successive one-electron transfer reactions at electrode surface in acidic solution. Previous reports on the electrochemical oxidation of other phenol molecules support the latter interpretation of sequential one-electron transfer (Lund and Hammerich, *Organic Electrochemistry*, 4$^{th}$ Revised and Expanded Revision, Marcel Dekker, Inc, New York, 2001), which is hereby incorporated by reference in its entirety). In physiological solution (pH7), no oxidation wave was observed in the first forward scan (FIG. 25, dashed line). However, a reduction peak appeared in the reverse scan, indicating the formation of an electrochemically active film on the electrode surface (lower dashed line -0.1 i/μA). In the second scan (red curve), an oxidation peak of the reduced film was observed (0.1 i/nA), and the reverse scan presents an increasing reduction peak.

Based on these mechanistic studies on the oxidation of DIPP on graphite microelectrode surfaces, new protocols were developed for its electrochemical quantification in acidic and physiologic solutions. Both methods have an order of magnitude better (lower) detection limit than the method of Example 1 ($1\times10^{-6}$M), which should permit the quantitative measurement of Propofol over the entire therapeutic and sub-therapeutic range of the drug. In addition, the microelectrode method is simpler and faster.

Figure 26A:
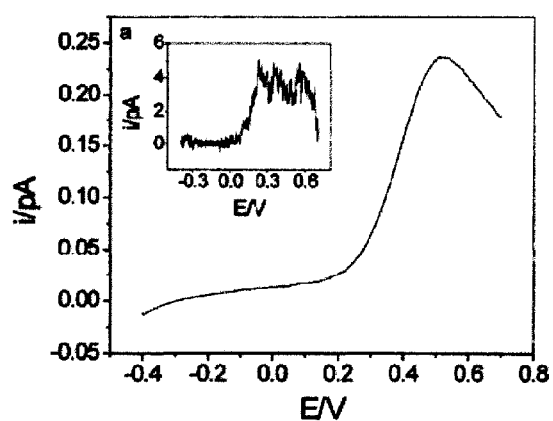
FIGS. 26A-B are a pair of graphs that illustrate the stripping analysis of Propofol in 0.01M pH7.0 HEPES solution: (a) the background-corrected stripping voltammograms for 0.1 mM and 1 µM Propofol (inset), and (b) the calibration curve of Propofol from 1.0 µM to 0.1 mM.
Figure 26B:
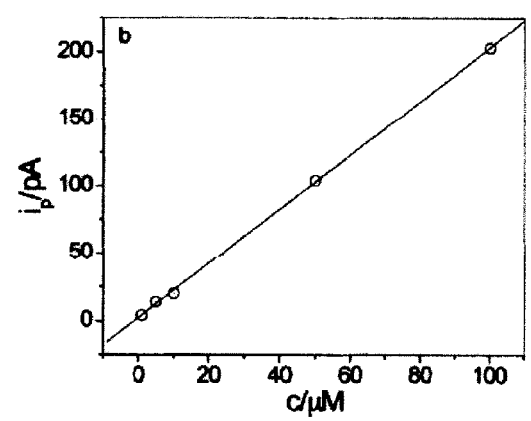

To evaluate the feasibility of detecting Propofol in a physiological environment using the carbon fiber microdisc electrode, Propofol was detected in 0.01 M pH 7.0 HEPES solution by stripping analysis. In this assay, the potential was held at 0.8V for 30 s to accumulate the conductive components, and then the potential was switch to -0.4V for 10 s to reduce the conductive film. The potential was scanned from -0.4 V to 0.65 V at 0.1V/s right after the reduction. 1 μM Propofol can be detected by this method, which is ~1 magnitude lower than the target therapeutic concentration in the blood (FIG. 26).

Measurement of DIPP in acidic solutions is relatively simple and fast. Electrode fouling does occur as was observed in Example 1, but multiple measurements can be made using a single microelectrode. DIPP can be measured in neutral solutions, but requires a "stripping" measurement. First, the electrode potential is set to a certain value for a short period of time (e.g., 2-3 minutes). During this time an oxidation product is collected on the electrode surface. Next, the electrode potential is set to the value at which the accumulated film is stripped off. It is somewhat slower, but the detection limit can be improved if the collection time is increased.

DIPP can also be measured in alkaline solutions; however, the electrode fouling is greater under alkaline conditions. In repeated experiments, the measured signal declines rapidly from its original value and the electrode surface must be renewed after each experiment. Due to the large mass transfer rate on the carbon microelectrode, problems related to the electrode fouling during the electrochemical measurement of DIPP significantly decreased relative to the macroelectrode. However, the decreasing current values indicate changes in the electrode surface properties, which make the method inadequate for the continuous in-line monitoring of DIPP levels for extended periods of time. Instead of continuous monitoring, serial measurements can be performed using individually addressable electrode arrays. By integrating such array sensors into a small volume flow through manifold the DIPP concentrations could be measured semi-continuously. Since each measurement will be performed on a different, single-use electrode, biofouling should not influence the analytical results.

Example 3—Carbon Nanofiber Sensor Array and Use for Propofol Detection

A prototype carbon nanofiber (CNF) array containing a chambered carbon nanofiber electrochemical sensor arrays with 40 individually addressable fibers was obtained from Oak Ridge National Laboratory. The array was prepared using known techniques (Guillorn et al., "Individually Addressable Vertically Aligned Carbon Nanofiber-based Electrochemical Probes," *J. Appl. Phys.* 91: 3824 (2002); McKnight et al., "Effects of Microfabrication Processing on the Electrochemistry of Carbon Nanofiber Electrodes," *J Phys Chem B* 107(39):10722-10728 (2003), each of which is hereby incorporated by reference in its entirety). Each fiber in the array can be individually queried and the electrochemical signal assessed. The reproducibility and performance of selected fibers within the array was tested in ferrocene methanol solution. Signals obtained from selected CNFs were similar and summed appropriately when the currents were added together.

Figure 27:
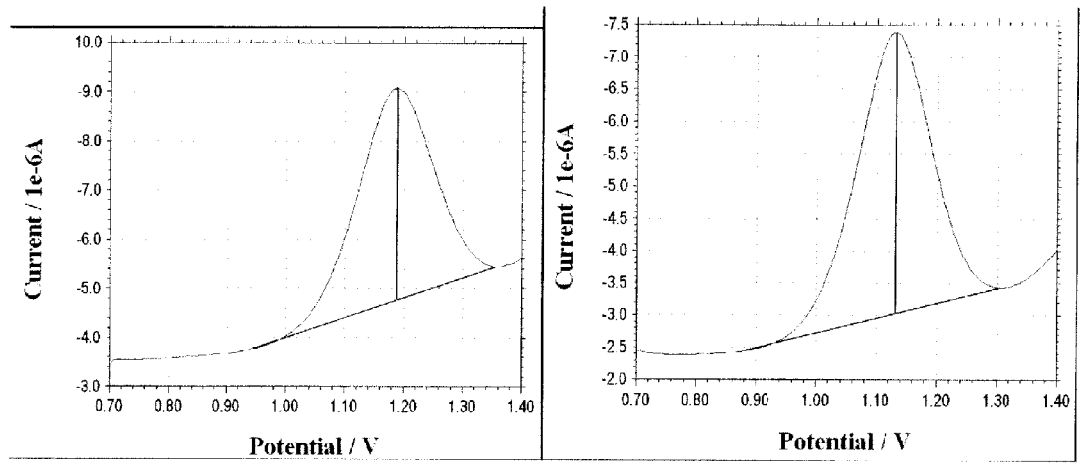
FIG. 27 is a pair of graphs illustrating signal intensity variances between different fibers in a CNF array.

The reproducibility and performance of selected fibers within the array was tested in ferrocene methanol solution (FIG. 27). Signals obtained from selected CNFs were similar and summed appropriately when the currents were added together. Some variance between CNFs was present within the array and represented differences in the final surface areas of the fibers, which are grown using a carbon sputtering method. The variances within the array demonstrate the need for measuring the signal of each CNF fiber relative to a reference electrode for calibration.

$Cl^-$ ion and bovine serum albumin ("BSA") interfere the voltammetric response of DIPP in pH 7 solutions at their blood concentrations. Unlike $Cl^-$ which alters the current response in a small range, BSA forms nonconductive polymers with the oxidation product of DIPP on the electrode surface and totally blocks the electrode. The fouling of electrodes and the interference from $Cl^-$ ion and BSA are obstacles to achieve a continuous monitor of the concentration of DIPP in plasma, serum or blood. A few solutions are considered. One of them is to extract and detect DIPP in organic solvent.

This idea is based on the facts that DIPP and its oxidation product have higher solubility in organic solvents, and even the mechanism of redox reaction can be different to that in aqueous solution. The fouling of electrodes may be avoidable in organic solvents. By extracting and detecting DIPP in organic solvent, $Cl^-$ ion and BSA interference in aqueous solution will also be eliminated. To check the feasibility of this idea, voltammetric response of DIPP has been investigated in acetonitrile, the most frequently used organic solvent in electrochemistry study.

Figure 28:
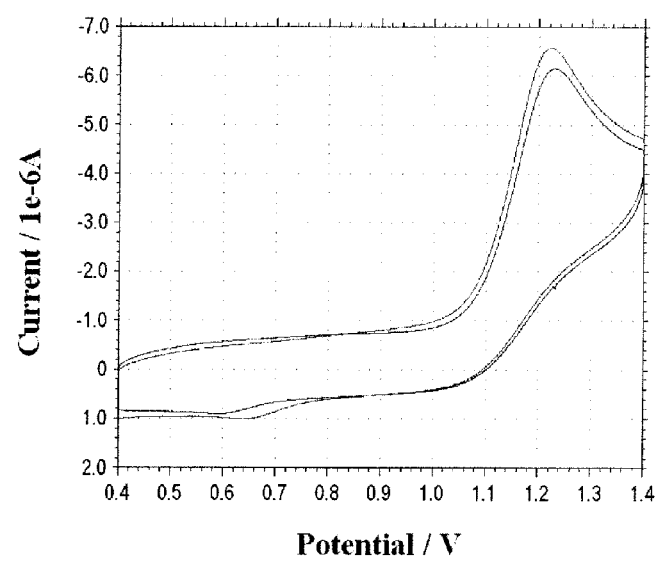
FIG. 28 is a cyclic voltammogram on a GC electrode in organic solution. No significant fouling is seen.

On carbon fiber microelectrode, the electrode fouling still happened in a $10^{-4}$M DIPP acetonitrile solution containing 0.1 M $TBAClO_4$ as supporting electrolyte. But the glassy carbon macroelectrode gave excellent results. Red and blue lines are the first and eighteenth scans, respectively (FIG. 28). A diffusive oxidation peak was observed, and the peak current decay seen after eighteen scans is very small (~7%). The comparison of diffusive peak in acetonitrile solution and surface-confined peak in aqueous solution suggest a different reaction mechanism.

Example 4—Glassy Carbon PVC-Coated Electrode and Use for Propofol Detection

The carbon microelectrodes currently in use were manufactured by lithography methods and by hand fabrication of an electrochemical cell for this purpose. In this design, three microelectrodes were sealed into three glass capillaries and combined into a 3-electrode array. The tip of the microelectrode array and the microfabricated alternative are shown (FIG. 29). The non-aqueous phase is a highly plasticized PVC film on the top of a three electrode electrochemical cell. The large surface Pt and Ag electrodes serve as counter and reference electrodes below the PVC membrane.

A PVC-oNPOE liquid membrane was used to coat the carbon electrode for an in situ extraction and detection phase. Briefly a thin PVC membrane containing o-NPOE and supporting electrolyte was spin-coated onto the top of a glassy carbon electrode. Measurements of DIPP were made in aqueous samples. The data from these studies strongly indicate that the PVC membrane actively partitions the organic DIPP molecule from solution and can be used to partition free (bioactive) drug from more complex solutions, without requiring an acidic environment. Based upon these findings, several EC sensor designs employing organic PVC-coated membranes were pursued.

Figure 30:
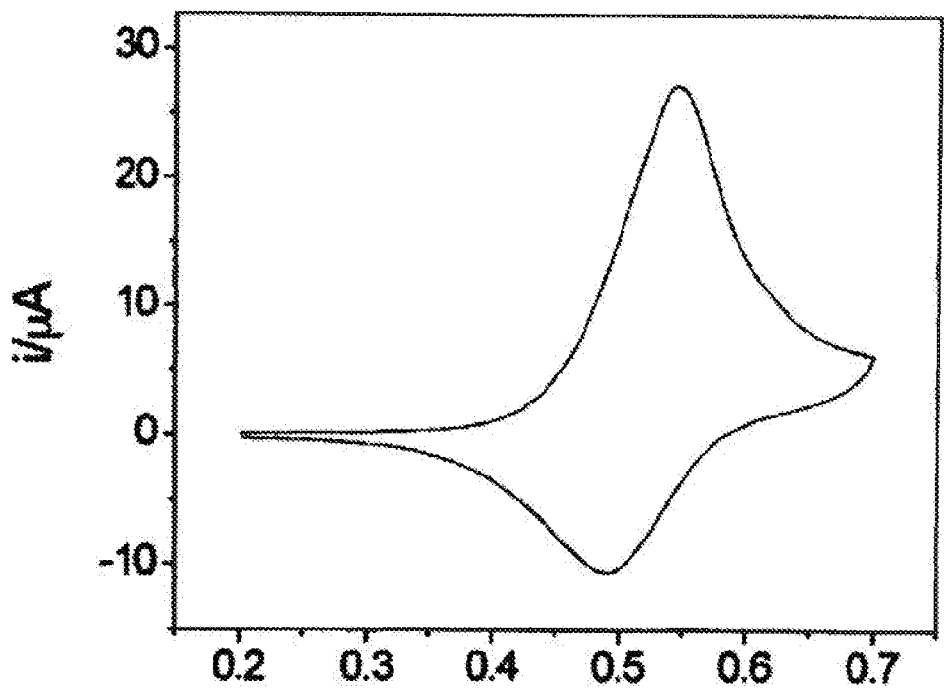
FIG. 30 is a cyclic voltammetry recorded with PVC-o-NPOE GC electrode in 0.5 mM FcMeOH and 8 mM $TBAClO_4$ solution.

The PVC cocktail, containing 18.0% PVC, 72.1% o-NPOE, and 9.9% tetradodecylammonium tetrakis(pentofluorophenyl)borate was prepared and drop cast on the GC electrode surface including the electrode site and insulator. The calculated thickness of the PVC membrane was ~3 microns. The electrode was first characterized in an aqueous solution contained 0.5 mM ferrocene methanol, 8 mM $TBAClO_4$ pH 7.2 PBS. The CV recorded shows a behavior similar to a thin-layer cell (FIG. 30). Considering the diffusion coefficient difference between the PVC membrane and the aqueous solution, the high peak current indicated that the partition coefficient between these two phases is very high. The reverse peak is smaller then the forward peak, which may be caused by the ferrocinium ion transfer at the PVC/water interface during the oxidation of ferrocene methanol.

Figure 31:
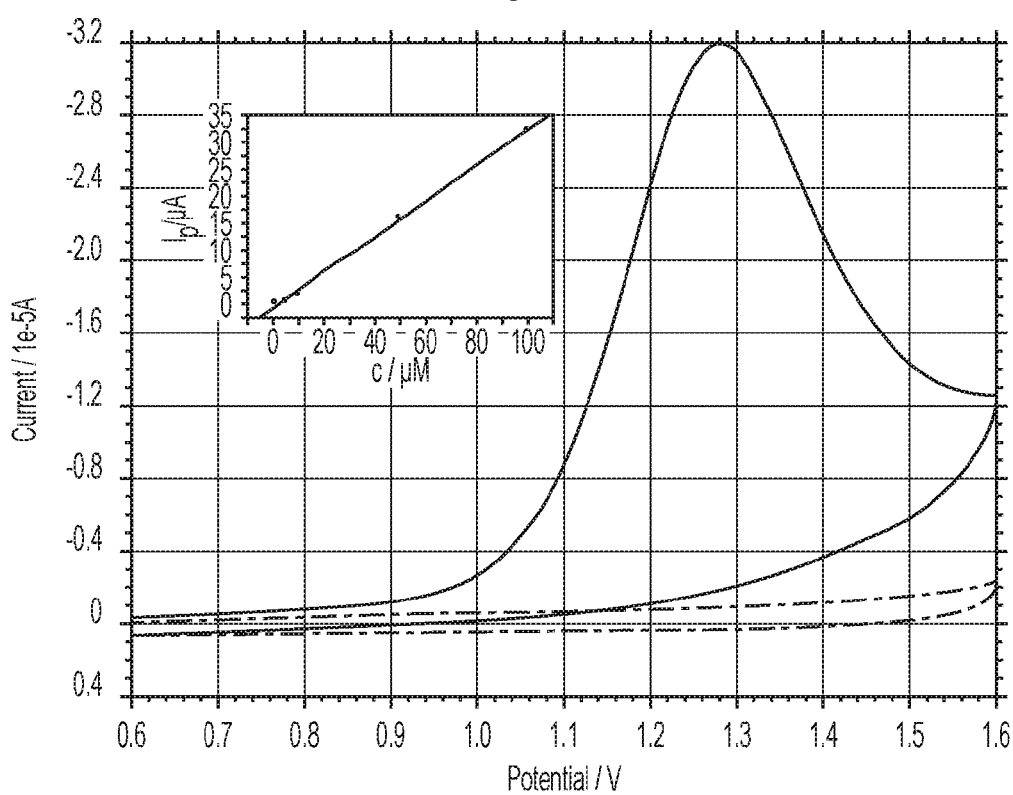
FIG. 31 is a cyclic voltammetry recorded with PVC-o-NPOE membrane-coated GC electrode in x mM Propofol+8 mM TBAClO4 pH 7.2 PBS solution (red line). The inset graph shows the calibration curve of DIPP from 104 to 0.1 mM in the same background solution.

Similar to its solubilized behavior in ferrocene methanol, hydrophobic Propofol is extracted from the aqueous phase into the PVCoNPOE organic layer on the PVC-coated EC sensor and is detected. FIG. 31 shows the CV of Propofol on a 3 μm-thick organic film-covered GC electrode. The aqueous solution contained $10^{-4}$ M DIPP and 8 mM $TBAClO_4$ and 0.1M phosphate buffer (pH 7.2). CV of DIPP (red line) was recorded on the GC electrode. The blue line is the background CV for the control experiment. The calibration curve from a DIPP concentration of $10^{-6}$M to $10^{-4}$M is shown in the inset and demonstrates a linear concentration/signal relationship.

Example 5—Glassy Carbon PVC-Coated Electrode and Affect of Interfering Agents on Propofol Detection Previous work detecting DIPP in aqueous solutions showed that in the presence of 0.12M NaCl, the anodic peak currents of the conductive film are much lower than those which were used to determine DIPP concentration. This shows that $Cl^-$ ion is interfering for the detection of DIPP in pH 7.0 solutions. In addition, in the presence of 4% bovine serum albumin (BSA) in vitro, the anodic current is smaller, and the cathodic and anodic currents of the conductive film were not observed. This implied that the oxidation product may react with the albumin and form a passive film on the electrode surface, which eventually blocks the electrode surface.

Based on these prior results with uncoated sensors, the PVC-coated EC sensors was screened to assess the affect of these interfering agents on sensor function for Propofol detection.

Figure 32:
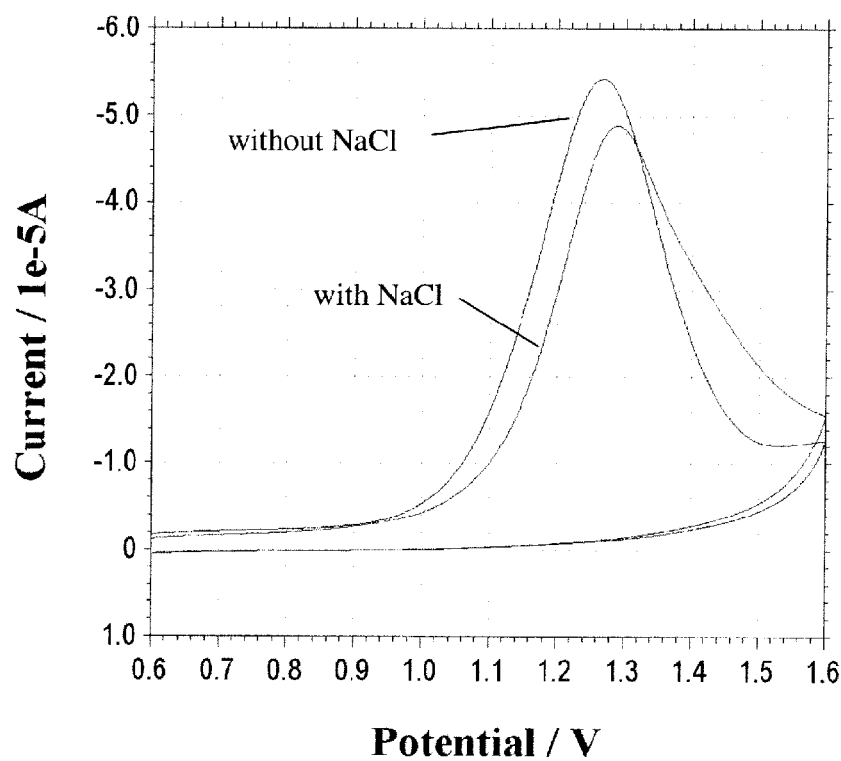
FIG. 32 is a cyclic voltammetry of 0.1M DIPP recorded with (red line) and without (blue line) 0.12M NaCl, with 8 mM $TBAClO_4$ and 0.1M PBS (pH 7.2).

Significant chloride ion interference was observed in the assay with a bare GC electrode in aqueous solution, where $Cl^-$ oxidation current appears in the same potential range where DIPP is detected. In the presence of the organic film (PVC-covered GC electrode), DIPP is extracted into the interference is not observed. The CV of DIPP on thin PVC film-covered GC electrodes in the presence of 0.12 M NaCl (red line) and the absence of chloride ion (blue line) are compared in FIG. 32. Other components in the solution are indicated above. These data demonstrate that by employing the thin organic film-covered GC electrodes, the chloride ion interference is essentially eliminated.

Figure 33:
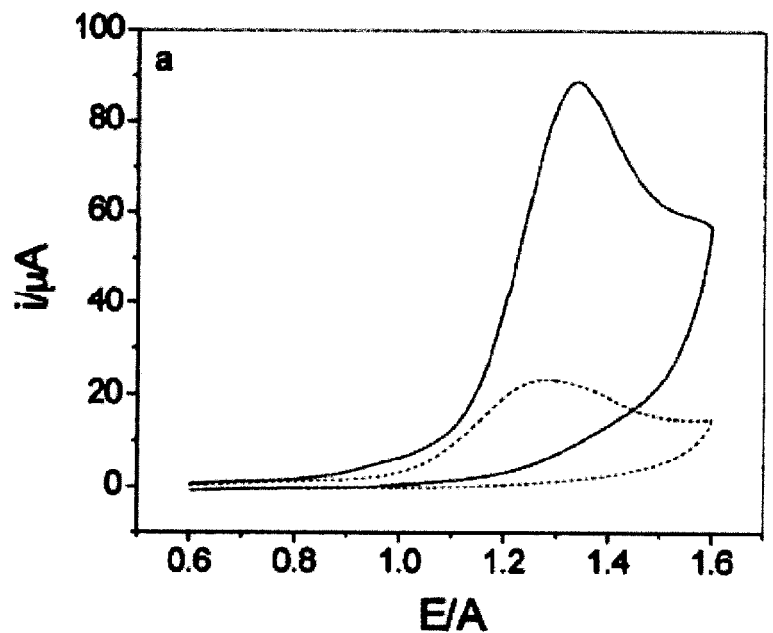
FIG. 33 is a cyclic voltammetry of 0.1M DIPP recorded with (dashed line) and without (solid line) 4% BSA.

Bovine serum albumin (BSA) was found to react with the oxidation product of Propofol and form a passivation layer on the GC electrode in aqueous solution. This passivation layer hindered the successive heterogeneous electron transfer reaction at the electrode/solution interface, and no faraday current for DIPP oxidation was observed. A form of BSA interference was also detected during DIPP detection using thin PVC-o-NPOE film-covered GC electrodes (FIG. 33). Specifically, a decrease in the peak current seen in CV was observed with $10^{-4}$M DIPP solution containing 4% BSA.

Figure 34:
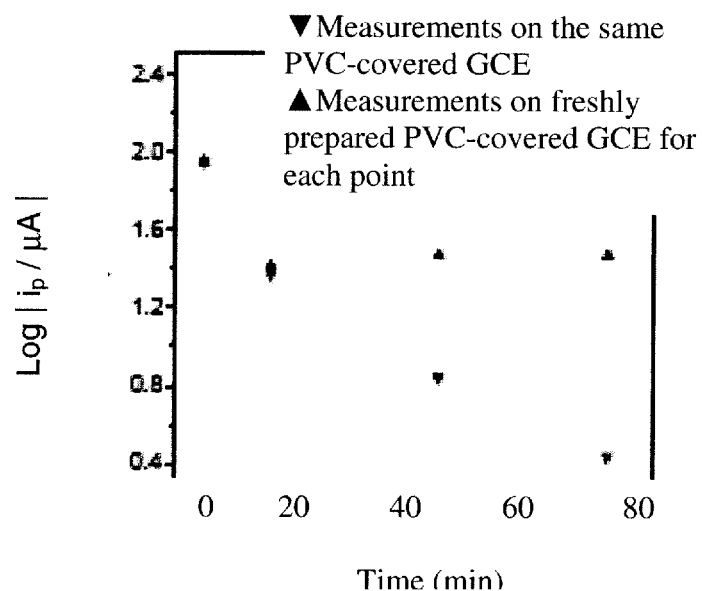
FIG. 34 is a graph showing the change in peak current over time in DIPP solution with 4% BSA. Maintained (red) or fresh GC electrode (blue) data are shown for comparison.

In FIG. 34, the time presents the mixing time of BSA and DIPP, and the data at t=0 are from a solution without BSA. The electrode for the measurements of the red points was kept in the stirred solution, while for the blue points a freshly prepared PVC-covered GC electrode was put into the stirred solution 12 min prior to the measurements. The comparison demonstrates that the decreasing current is caused by the adsorption of BSA at the organic/water interface, instead of the binding of DIPP to BSA in aqueous solution. To maintain the oxidation current at GC/organic interface, an anion transfer from the aqueous to organic phase or a cation transfer from organic to aqueous phase is required. In this system, perchlorate ions transfer across the organic/water interface. The adsorbed BSA layer, which is negatively charged at pH 7.2, can hinder the anion transfer, resulting in a reduced current.

Figure 35:
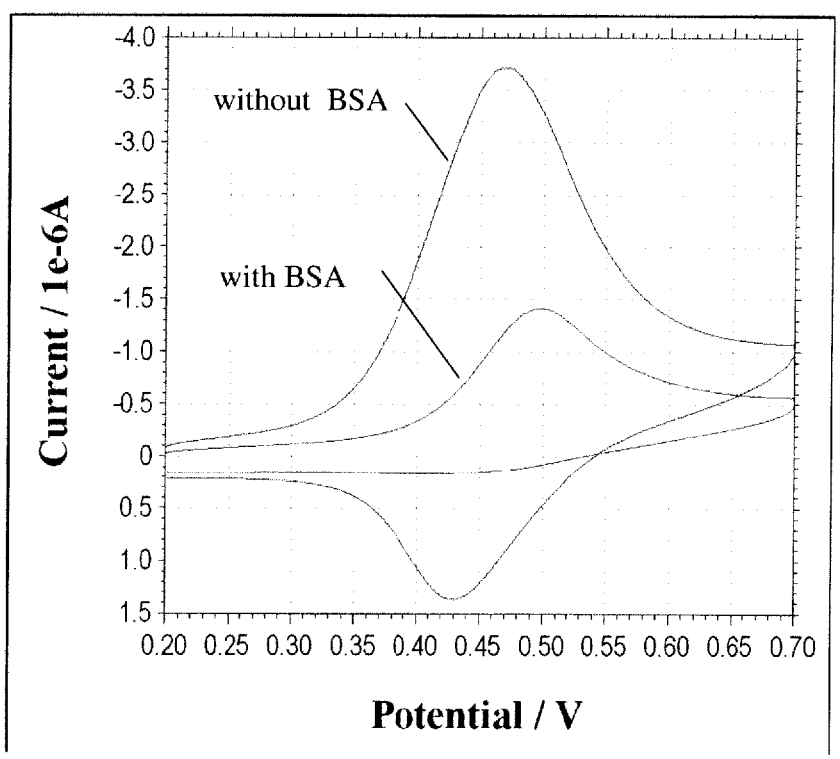
FIG. 35 is a cyclic voltammetry of 0.1M ferrocene methanol in the absence (blue line) or in the presence of 4% BSA (red line).

To verify the mechanism of BSA interference, the CVs of ferrocenemethanol (FcMeOH) on a PVC-o-NPOE-covered GC electrode were compared in the presence (FIG. 35, red line) and in the absence of 4% BSA (FIG. 35, blue line), after 12 min stirring. In the absence of BSA, FcMeOH is oxidized at GC electrode surface and generated a cation product methanol-ferrocenium, which is relatively hydrophilic, and can diffuse to the organic/water interface and transfer into aqueous phase. The much smaller reverse peak confirms the loss of ferrocenium ions from the organic phase. In this case, the electronic current at GC/organic interface was compensated by the ionic current from perchlorate ions transfer from aqueous phase to organic phase and ferrocenium ions transfer from organic phase to aqueous phase. In the presence of BSA, the absorbed BSA layer hinders the anion transfer, so that the ferrocenium ions contribute more in the ionic current competition. As a consequence, the reduction peak of ferrocenium ion almost disappears.

There are several solutions to the BSA interference problem based on this mechanism. One approach is to apply a size-exclusion layer with negligible BSA adsorption on top of PVC membrane to diminish the BSA adsorption. An alternative to this is eliminating the need for an ionic current across the organic/water interface. This can be achieved when the entire electrochemical cell is arranged within the organic phase. In the current system, the working electrode was in the organic phase, but the reference and counter electrodes were in the aqueous phase. If all the three electrodes are arranged in the organic phase, there is no requirement of ionic current at organic/water interface to maintain the electronic current at GC/organic interface. By using an electrochemical cell in which all three electrodes are in the organic phase, it will not be necessary to add perchlorate ions in the sample solution as in the experiments with the PVC membrane coated GC electrode.

Figure 36:
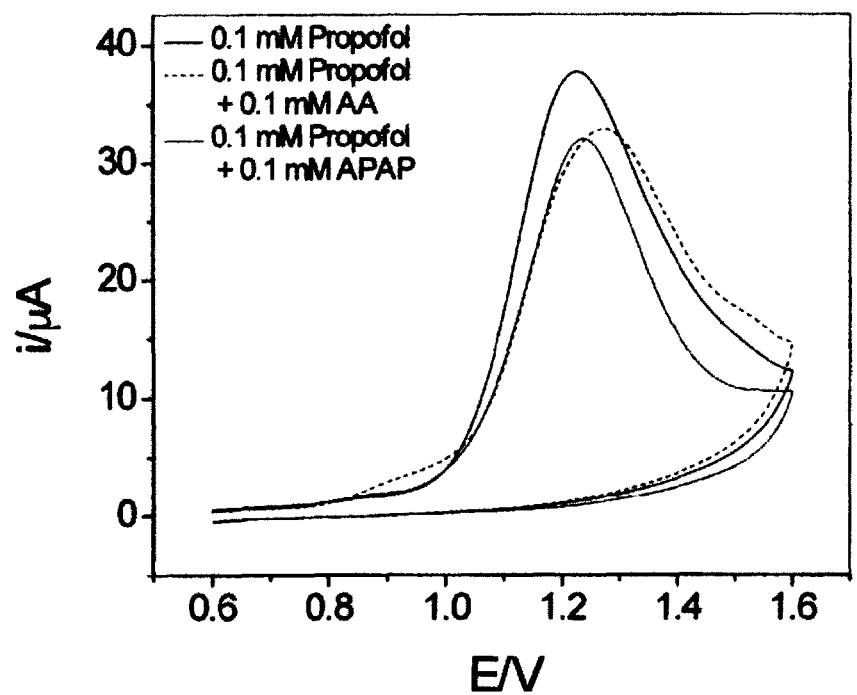
FIG. 36 is a cyclic voltammetry of 0.1 mM DIPP in the absence of interference (solid line), or in the presence of 0.1 mM ascorbate (dashed line) or 0.1 mM N-acetyl-p-aminophenol (dotted line).

Due to the similarity in molecular structure between Propofol and the commonly used vitamin ascorbate (Vitamin C) and the pain reliever Tylenol® (N-acetyl-p-aminophenol, acetaminophen,) in clinical medicine, the potential for these compounds to interfere with the detection of free Propofol in solution was determined using CV methods. The interference from Vitamin C and Tylenol® were evaluated by adding 0.1 mM ascorbate or 0.1 mM N-acetyl-p-aminophenol to the sample solution with 0.1 mM DIPP, respectively. The presence of these two compounds slightly decreased (~10%) the anodic current of Propofol (FIG. 36). However, this does not create a practical problem in the application of EC Propofol sensing in the clinical environment where Tylenol®, in particular, is commonly used.

Example 6—Construction of Microfluidic Sensor Array

An ex-vivo glass slide biosensor with incorporated measuring and reference electrodes was fabricated using electrode patterning techniques followed by a covering formed with a polyimide insulation. Polydimethylsiloxane (PDMS) based microfluidic channels were then formed over sections of the chip, creating three distinct sampling stations on a single chip. The electrodes are larger than the channel defined by the PDMS covering, making the alignment of the channel easier.

According to one design, the electrode assembly is in the form of a microelectrode array (MEA) that includes 5 µm diameter gold discs that are spaced 50 µm center-to-center and hexagonally arranged (FIG. 37). This microfluidic array device has been fabricated and is suitable for detection of bioavailable Propofol.

According to another design, the electrode assembly is in the form of a microband electrode array that includes 5 µm wide individually addressable bands, 100 µm center-to-center distance (FIG. 38). The bands can optionally be interconnected with a single lead wire like the MEAs. This microfluidic array device has been fabricated and is suitable for detection of bioavailable Propofol.

According to another design, the electrode assembly is in the form of an interdigitated electrode array with 5 µm wide fingers and 5 µm wide gaps (FIG. 39). This microfluidic array device has been fabricated and is suitable for detection of bioavailable Propofol.

The glass slide design can be further optimized by converting to a silicone wafer-based platform. Such chip-based EC platforms can be produced in a cost effective manner and cast with microfluidic manifolds. An example of the wafer being used to fabricate our chip-based designs will permit fabrication of 9 sensors from each wafer.

All of the features described herein (including any accompanying claims, abstract and drawings), and/or all of the steps of any method or process so disclosed, may be combined with any of the above aspects in any combination, except combinations where at least some of such features and/or steps are mutually exclusive.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. Additionally, the recited order of processing elements or sequences, or the use of numbers, letters, or other designations therefore, is not intended to limit the claimed processes to any order except as may be specified in the claims. These alterations, improvements, and modifications are intended to be suggested hereby, and are within the spirit and scope of the invention. Accordingly, the invention is limited only by the following claims and equivalents thereto.

What is claimed:

1. An electrochemical, voltammetric sensor device comprising:
   at least two or more electrodes and a water-immiscible coating that surrounds the electrodes,
   wherein the water-immiscible coating is in contact with the electrodes, wherein the water-immiscible coating comprises about 15 to about 67 wt percent polyvinylchloride (PVC), about 33 to about 85 wt percent 2-nitrophenyl octal ether (o-NPOE), and about 0.001 to about 15 wt percent tetradecylammonium tetrakis (pentoflurorphenyl)borate (TDATPFPB),
   wherein the water-immiscible coating partitions a hydrophobic drug from a fluid sample wherein the partitioned drug is oxidized within the water-immiscible coating, wherein the electrodes measure an oxidation/reduction current within the water-immiscible coating, and wherein the measured oxidation/reduction current indicates the concentration of a drug in the fluid sample.

2. The electrochemical, voltammetric sensor device of claim 1, wherein the electrodes comprise a working electrode, a reference electrode, a counter electrode, or any combination thereof.

3. The electrochemical, voltammetric sensor device of claim 2, wherein the working electrode comprises glassy carbon, the reference electrode is composed of silver, and the counter electrode comprises platinum.

4. An electrochemical, voltammetric sensor device comprising:
   two or more electrodes and a water-immiscible coating that surrounds the electrodes, wherein the water-immiscible coating is in contact with the electrode and comprises about 15 to about 67 wt percent polyvinylchloride (PVC), about 33 to about 85 wt percent 2-nitrophenyl octyl ether (o-NPOE), and about 0.001 to about 15 wt percent tetradecylammonium tetrakis (pentoflurorphenyl)borate (TDATPFPB).

5. The electrochemical, voltammetric sensor device of claim 4, wherein the two or more electrodes comprise a glassy carbon working electrode, a silver reference electrode, a platinum counter electrode, or any combination thereof.

6. A catheter comprising: a body and a lumen, and an electrochemical, voltammetric sensor device according to claim 1 or 4 in communication with the lumen or externally of the body, wherein the water-immiscible coating is capable of partitioning a bioavailable drug directly from a body fluid.

7. A micro fluidic device comprising a micro fluid channel and an electrochemical, voltammetric sensor device according to claim 1, or 4 in communication with the microfluid channel.

* * * * *